US006961664B2

(12) United States Patent
Selifonov et al.

(10) Patent No.: US 6,961,664 B2
(45) Date of Patent: *Nov. 1, 2005

(54) METHODS OF POPULATING DATA STRUCTURES FOR USE IN EVOLUTIONARY SIMULATIONS

(75) Inventors: Sergey A. Selifonov, Los Altos, CA (US); Willem P. C. Stemmer, Los Gatos, CA (US)

(73) Assignee: Maxygen, Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 19 days.

(21) Appl. No.: 09/495,668

(22) Filed: Feb. 1, 2000

(65) Prior Publication Data

US 2003/0032010 A1 Feb. 13, 2003

Related U.S. Application Data

(63) Continuation of application No. PCT/US00/01138, filed on Jan. 18, 2000, which is a continuation-in-part of application No. 09/494,282, filed on Jan. 18, 2000, and a continuation-in-part of application No. PCT/US00/01202, filed on Jan. 18, 2000, and a continuation-in-part of application No. 09/484,850, filed on Jan. 18, 2000, now Pat. No. 6,368,861, and a continuation-in-part of application No. PCT/US00/01203, filed on Jan. 18, 2000, and a continuation-in-part of application No. 09/416,837, filed on Oct. 12, 1999, now abandoned, which is a continuation-in-part of application No. 09/416,375, filed on Oct. 12, 1999, now abandoned, which is a continuation-in-part of application No. 09/408,392, filed on Sep. 28, 1998, now Pat. No. 6,376,346.

(60) Provisional application No. 60/141,049, filed on Jun. 24, 1999, provisional application No. 60/118,813, filed on Feb. 5, 1999, provisional application No. 60/118,854, filed on Feb. 5, 1999, and provisional application No. 60/116,447, filed on Jan. 19, 1999.

(51) Int. Cl.[7] .................. G01N 33/48; G01N 31/00; C12Q 1/68; C07H 21/02
(52) U.S. Cl. ..................... 702/19; 435/6; 536/23.1; 702/27
(58) Field of Search .................. 435/6; 536/23.1; 702/19, 27; 706/47; 712/200

(56) References Cited

U.S. PATENT DOCUMENTS

| | | |
|---|---|---|
| 4,959,312 A | 9/1990 | Sirokin |
| 4,994,379 A | 2/1991 | Chang |
| 5,023,171 A | 6/1991 | Ho et al. |
| 5,043,272 A | 8/1991 | Hartly et al. |
| 5,066,584 A | 11/1991 | Gyllensten et al. |
| 5,264,563 A | 11/1993 | Huse |
| 5,319,308 A | 6/1994 | Dechene |
| 5,408,181 A | 4/1995 | Dechene |
| 5,447,839 A | 9/1995 | Manos et al. |
| 5,512,463 A | 4/1996 | Stemmer |
| 5,514,588 A | 5/1996 | Varadaraj et al. |
| 5,519,319 A | 5/1996 | Smith |
| 5,521,077 A | 5/1996 | Kholsa et al. |
| 5,565,350 A | 10/1996 | Kmiec |
| 5,580,730 A | 12/1996 | Okamoto |
| 5,603,793 A | 2/1997 | Yoshida et al. |
| 5,605,793 A | 2/1997 | Stemmer |
| 5,612,205 A | 3/1997 | Kay et al. |
| 5,650,722 A | 7/1997 | Smith |
| 5,675,253 A | 10/1997 | Smith |
| 5,717,085 A | 2/1998 | Little et al. |
| 5,760,012 A | 6/1998 | Kmiec et al. |
| 5,763,239 A | 6/1998 | Short et al. |
| 5,789,228 A | 8/1998 | Lam et al. |
| 5,789,577 A | 8/1998 | Geysen |
| 5,811,238 A | 9/1998 | Stemmer et al. |
| 5,814,473 A | 9/1998 | Warren et al. |
| 5,824,469 A | 10/1998 | Horwitz et al. |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minshull et al. |
| 5,866,363 A | 2/1999 | Pieczenik |
| 5,869,644 A | 2/1999 | Shortle et al. |

(Continued)

FOREIGN PATENT DOCUMENTS

| | | |
|---|---|---|
| EP | 0911396 A2 | 4/1999 |
| EP | 0911396 A3 | 5/1999 |
| EP | 0934999 A1 | 8/1999 |

(Continued)

OTHER PUBLICATIONS

Yokomori et al., "A similarity measure for DNA sequence analysis based on locality," Genome Inf. Ser. (1993), vol. 4, pp. 283–292.*

Sun, Fengzhu, "Modeling DNA Shuffling," Journal of Computational Biology, 1999, vol. 6, No. 1, pp. 77–89.*

Merriam–Webster On–line Dictionary, 2002, www.m–w.com.*

(Continued)

*Primary Examiner*—Kenneth R. Horlick
*Assistant Examiner*—Young J. Kim
(74) *Attorney, Agent, or Firm*—Sharon M. Fujita; Jeffrey K. Weaver; Norman J. Kruse

(57) ABSTRACT

In particular, this invention provides novel methods of populating data structures for use in evolutionary modeling. In particular, this invention provides methods of populating a data structure with a plurality of character strings. The methods involve encoding two or more a biological molecules into character strings to provide a collection of two or more different initial character strings; selecting at least two substrings from the pool of character strings; concatenating the substrings to form one or more product strings about the same length as one or more of the initial character strings; adding the product strings to a collection of strings; and optionally repeating this process using one or more of the product strings as an initial string in the collection of initial character strings.

157 Claims, 7 Drawing Sheets

U.S. PATENT DOCUMENTS

| | | |
|---|---|---|
| 5,876,997 A | 3/1999 | Kretz |
| 5,912,119 A | 6/1999 | Radman et al. |
| 5,925,749 A | 7/1999 | Mathur et al. |
| 5,928,905 A | 7/1999 | Stemmer et al. |
| 5,939,250 A | 8/1999 | Short |
| 5,939,300 A | 8/1999 | Robertson et al. |
| 5,942,430 A | 8/1999 | Robertson et al. |
| 5,948,666 A | 9/1999 | Callen et al. |
| 5,958,672 A | 9/1999 | Short |
| 5,958,751 A | 9/1999 | Murphy et al. |
| 5,962,258 A | 10/1999 | Mathur et al. |
| 5,962,283 A | 10/1999 | Warren et al. |
| 5,965,408 A | 10/1999 | Short |
| 5,985,646 A | 11/1999 | Murphy et al. |
| 6,001,574 A | 12/1999 | Short et al. |
| 6,004,788 A | 12/1999 | Short |
| 6,030,779 A | 2/2000 | Short |
| 6,054,267 A | 4/2000 | Short |
| 6,096,548 A | 8/2000 | Stemmer |
| 6,117,679 A | 9/2000 | Stemmer |
| 6,125,331 A | 9/2000 | Toh |
| 6,132,970 A | 10/2000 | Stemmer |
| 6,153,410 A | 11/2000 | Arnold et al. |
| 6,159,690 A | 12/2000 | Borrebaeck et al. |
| 6,188,965 B1 | 2/2001 | Mayo et al. |
| 6,269,312 B1 | 7/2001 | Mayo et al. |
| 6,403,312 B1 | 6/2002 | Dahiyat et al. |
| 6,455,254 B1 | 9/2002 | Short |
| 6,537,776 B1 | 3/2003 | Short |
| 6,605,449 B1 | 8/2003 | Short |

FOREIGN PATENT DOCUMENTS

| | | |
|---|---|---|
| WO | WO 91/06643 A1 | 5/1991 |
| WO | WO 92/06176 | 4/1992 |
| WO | WO 95/15972 | 6/1995 |
| WO | WO 95/22625 | 8/1995 |
| WO | WO 96/16073 A2 | 5/1996 |
| WO | WO 96/16073 A3 | 5/1996 |
| WO | WO 96/33207 | 10/1996 |
| WO | 97/07205 | 2/1997 |
| WO | 97/20078 | 6/1997 |
| WO | 97/25410 | 7/1997 |
| WO | WO 97/33957 | 9/1997 |
| WO | 97/35957 | 10/1997 |
| WO | 97/35966 | 10/1997 |
| WO | WO 97/35966 | 10/1997 |
| WO | 97/44361 | 11/1997 |
| WO | 97/48416 | 12/1997 |
| WO | 97/48717 | 12/1997 |
| WO | 97/48794 | 12/1997 |
| WO | 98/00526 | 1/1998 |
| WO | 98/01581 | 1/1998 |
| WO | 98/13485 | 4/1998 |
| WO | 98/13487 | 4/1998 |
| WO | 98/24799 | 6/1998 |
| WO | 98/27230 | 6/1998 |
| WO | 98/28416 | 7/1998 |
| WO | 98/31387 | 7/1998 |
| WO | 98/36080 | 8/1998 |
| WO | 98/41622 | 9/1998 |
| WO | 98/41623 | 9/1998 |
| WO | 98/41653 | 9/1998 |
| WO | 98/42832 | 10/1998 |
| WO | 98/48034 | 10/1998 |
| WO | WO 98/49350 | 11/1998 |
| WO | 98/58085 | 12/1998 |
| WO | 99/07837 | 2/1999 |
| WO | 99/08539 | 2/1999 |
| WO | 99/10472 | 3/1999 |
| WO | 99/10539 | 3/1999 |
| WO | 99/19518 | 4/1999 |
| WO | 99/21979 | 5/1999 |
| WO | 99/23107 | 5/1999 |
| WO | 99/23236 | 5/1999 |
| WO | 99/41368 | 8/1999 |
| WO | 99/41369 | 8/1999 |
| WO | 99/41383 | 8/1999 |
| WO | 99/41402 | 8/1999 |
| WO | 99/45154 | 9/1999 |
| WO | 99/57128 | 11/1999 |
| WO | 99/65927 | 12/1999 |
| WO | WO 00/00632 | 1/2000 |
| WO | WO 00/23564 A2 | 4/2000 |
| WO | 00/37684 | 6/2000 |
| WO | WO00/42559 | 7/2000 |
| WO | WO 00/42560 | 7/2000 |
| WO | WO 00/42561 | 7/2000 |
| WO | WO00/47612 | 8/2000 |
| WO | WO 00/53744 | 9/2000 |
| WO | WO 00/58517 | 10/2000 |
| WO | WO01/61344 | 8/2001 |
| WO | WO01/75767 | 10/2001 |

OTHER PUBLICATIONS

Dahiyat et al., "*Automated Design of the Surface Positions of Protein Helices.*" Protein Science 1997, pp. 1333–1336.

Dahiyat et al., "*De Novo Protein Design: Fully Automated Sequence Selection,*" Science vol. 278 Oct. 3, 1997, pp. 82–87.

Dahiyat et al., "*De Novo Protein Design: Towards Fully Automated Sequence Selection,*" J. Mol. Biol. 1997 273, pp. 789–796.

Dahiyat et al., "*Probing the Role of Packing Specificity in Protein Design,*" Proc. Natl. Acad. Sci. USA, Sep. 1997, vol. 94, pp. 10172–10177.

Gordon and Mayo, "*Branch–and–Terminate: A Combinatorial Optimization Algorithm for Protein Design,*" Structure, Sep. 1999, pp. 1089–1098.

Gordon et al., "*Energy Functions for Protein Design,*" Current Opinion in Structural Biology, 1999, pp. 509–513.

Gordon and Mayo, "*Radical Performance Enhancements for Combinatorial Optimization Algorithms Based on the Dead–End Elimination Theorem,*" Journal of Computational Chemistry, 1998, vol. 19, pp. 1505–1514.

Haney et al., "*Structural Basis for Thermostability and Identification of Potential Active Site Residues for Adenylate Kinases From the Archaeal Genus Methanococcus,*" Proteins: Structure, Function, and Genetics, 1997, pp. 117–130.

Malakauskas and Mayo, "*Design, Structure and Stability of a Hyperthermophilic Protein Variant,*" Natural Structural Biology, Jun. 1998, vol. 5 No. 6, pp. 470–475.

Pollock et al., "*Coevolving Protein Residues: Maximum Likelihood Identification and Relationship to Structure,*" J. Mol. Biol, 1999, pp. 187–198.

Street and Mayo, "*Computation Protein Design,*" Structure, May 1999, pp. R105–R109.

Street and Mayo, "*Intrinsic β–sheet Propensities Result from van der Walls Interactions Between Side Chains and the Local Backbone,*" Proc. Natl. Acad. Sci. USA, Aug. 1999, vol. 96, pp. 9074–9076.

Street and Mayo, "*Pairwise Calculation of Protein Solvent–Accessible Surface Areas,*" Folding & Design, Jun. 3, 1998, pp. 253–258.

Strop and Mayo, "*Rubredoxin Variant Folds without Iron*," American Chemical Society, Mar. 24, 1999, vol. 121, No. 11, pp. 2341–2345.

Wollenberg and Atchley, "*Separation of Phylogenetic and Functional Associations in Biological Sequences by Using the Parametric Bootstrap*," PNAS, Mar. 28, 2000, vol. 97, pp. 3288–3291.

Stemmer, "*DNA Shuffling by Random Fragmentation and Reassembly: In Vitro Recombination for Moleclar Evolution*," Proc. Natl. Acad. Sci. USA, Oct. 1994, vol. 91, pp. 10747–10751.

Venkatasubramanian et al., "*Evolutionary Design of Molecules with Desired Properties Using the Genetic Algorithm*," J. Chem. Inf. Comput. Sci., 1995, vol. 35pp. 188–195.

Whipple et al., "*Application of Genetic Algorithms to Combinatorial Synthesis: A Computational Approach to Lead Identification and Lead Optimization*," J. AM. Chem. Soc., 1996, vol. 118, pp. 1669–1676.

Harayama, Shigeaki, "*Artificial Evolution by DNA Shuffling*," Tibtech, Feb. 1998, vol. 16, pp. pp. 16–19 and pp. 80–82.

Zhang, Ching, "*A Genetic Algorithm for Molecular Sequence Comparison*," Proceedings of the International Conference on Systems, Man, and Cybernetics, 1994, pp. 1926–1931.

Stemmer et al., "*Single–Step assembly of a Gene and Entire Plasmid from Large Numbers of Oligodeoxyribonucleotides*," Gene, 1995, vol. 164, pp. 49–53.

CS 262, Computational Genomics, Handout ™1: Course Information, printed from: http://www.stanford.edu/class/cs, Spring 2003, 11 pages.

Corpet et al., Browsing Protein Families Via the Rich Family Description Format, Bioinformatics, vol. 15, No. 12, 1999, pp. 1020–1027.

Mironov et al., "Computer Analysis of Transcription Regulatory Patterns in Completely Sequenced Bacterial Genomes," Nucleic Acids Research, vol. 27, No. 14, 1999, pp. 2981–2989.

Moore et al., *Modeling and Optimization of DNA Recombination*, Computer and Chemical Engineering 2000, Department of Chemical Engineering, The Pennsylvania State University, University Park © 2000.

Gregory L. Moore, Costas D. Maranas, *Modeling DNA Mutation and Recombination for Directed Evolution Experiments*, Department of Chemical Engineering, The Pennsylvania State University, University Park, Received Oct. 28, 1999, Accepted in revised form Apr. 15, 2000 © 2000 Academic Press.

Young et al., "Characterization of Receptor Binding Determinants of Granulocyte Colony Stimulating Factor," *Protein Science* 6:1228–1236, 1997.

Dahiyat and Mayo, "Protein Design Automation," Protein Science, 5:895–903, (1996).

Su et al., "Coupling Backbone Flexibility and Amino Acid Sequence Selection in Protein Design," Protein Science, 6:1701–1707, (1997).

Voigt et al., "Computationally Focusing the Directed Evolution of Proteins," Journal of Cellular Biochemistry Supplement, 37:58–63 (2001).

Hellberg et al., "Minimum Analogue Peptide Sets (MAPS) for Quantitative Structure–Activity Relationships," Int. J. Peptide Protein Res. 37:414–427 (1991).

Martin van Heel, "A New Family of Powerful Multivariates Statistical Sequence Analysis Techniques," J. Mol. Biol, 220:877–887 (1991).

Goldman et al., "Estimating Protein Function From Combinatorial Sequence Data Using Decision Algorithms and Neural Networks," Drug Dev. Research 33:125–132 (1994).

Gustafsson et al., "Exploration of Sequence Space for Protein Engineering," J. Mol. Recognit. 14:308–314 (2001).

Miyazawa et al., "Residue–Residue Potentials with a Favorable Contact Pair Term and an Unfavorable High Packing Density Term, for Simulation and Threading," J. Mol. Biol., 256:623–644 (1996).

Chao Zhang, "Extracting Contact Energies From Protein Structures: A Study Using a Simplified Model," Proteins: Structure, Function, and Genetics, 31:299–308 (1998).

Miyazawa et al., "Self–Consistent Estimation of Inter–Residue Protein Contact Energies Based on an Equilibrium Mixture Approximation of Residues," Proteins: Structure, Function, and Genetics, 34:49–68 (1999).

Miyazawa et al., "An Empirical Energy Potential With a References State for Protein Fold and Sequence Recognition," Proteins: Structure, Function, and Genetics, 36:357–369 (1999).

Moore et al., "Predicting Crossover Generation in DNS Shuffling," PNAS, vol. 98, No. 6, 3226–3231 (2001).

Lehman et al., "Engineering Proteins for Thermostability: the Use of Sequence Alignments Versus Rational Design and Directed Evolution," Current Opinion in Biotechnology, 13:371–375 (2001).

Colleen Kelly, "A Test of the Markovian Model of DNA Evolution," Biometrics 50, 653–664, (1994).

H.W. Hellinga, "Rational Protein Design: Combining Theory and Experiment," Proc. Natl. Acad. Sci. USA, vol. 94, pp. 10015–10017, (1997).

William F. DeGrado, "Proteins from Scratch," Science, vol. 278, 80–81 (1997).

Jonsson, et al, "Quaintitative Sequence–Activity Modeils (QSAM)– Tool For Sequence Design", Nuclear Acid Research vol. 21, No. 3, pp. 733–739 (1993).

Sjostrom, et al, "Signal Peptide Amino Acid Sequences in *Escheruchua coli* Contain Information Related To Final Protein Localization. A Multivariate Data Analysis", The CMBO Journal vol. 6, No. 3, pp 823–831, (1987).

Patel, et al, "Patenting Computer–Designed Peptides", Journal Of Computer–Acid Molecular Design 12 pp543–556, (1998).

Schneider, et al, "Peptide Design by Artificial Neural Networks and Computer–Based Evolutionary Search", Proc. Natl. Acad. Sci. USA, vol. 95, pp. 12179–121184, Oct. 1998.

Mee, et al, "Design of Active Analogues of a 15–Residue Peptide Using D–Optimal Design QSAR and a Combinatorial Search Algorithm", J Peptide Res. 49, pp. 89–102, (1997).

Bogarad, et al, "A Hierarchical Approach to Protein Molecular Evolution", Proc. Natl. Acad. Sci. USA, vol. 96, pp. 2597–2595, Mar. 1999.

Darius, et al, "Simulated Molecular Evolution" Or Computer–Generated Artifacts?, Biophysical Journal, vol. 67, pp. 2120–2122, Nov. 1994.

Martin et al., "Measuring Diversity: Experimental Design of Combinatorial Libraries for Drug Discovery," J. Med. Chem. 38, 1431–1436, 1995.

Sheridan et al., " Using a Genetic Algorithm to Suggest Combinatorial Libraries," J. Chem. Inf. Compu. Sci., 35, 310–320, 1995.

D.K. Agrafiotis, "Multiobjective Optimization of Combinatorial Libraries," IBM J. Res & Dev., vol., 45, No. 3, 545–566, 2001.

Selifonov, Sergey A. et al., "Methods For Making Characteristics Strings, Polynucleotides And Polypeptides Having Desired Characteristics", U.S. Appl. No. 09/416,375, filed Oct. 12, 1999.

Selifonov, Sergey A. et al, "Methods For Making Character Strings, Polynucleotides And Polypeptides Having Desired Characteristics", U.S. Appl. No. 09/494,282, filed Jan. 18, 2000.

Selifonov, Sergey A. et al., "Methods For Making Characteristics Strings, Polynucleotides And Polypeptides Having Desired Characteristics", U.S. Appl. No. 09/539,486, filed Mar. 30, 200.

Selifonov, Sergey A. et al., "Methods For Making Character Strings, Polynucleotides And Polypeptides Having Desired Characteristics", U.S. Appl. No. 09/618,579, filed Jul. 18, 2000.

Selifonov, Sergey A. et al. "Methods For Making Characteristics Strings, Polynucleotides And Polypeptides Having Desired Characteristics", PCT Application No. PCT/US00/01202, Publication No. WO 00/02560.

Selifonov, Sergey A. et al. "In Silico Cross–Over Selection", PCT Application No. PCT/US01/10231, Publication No. WO 01/75767 A3.

Alexeev et al. "Stable and Inheritable changes in genotype and phenotype of albino melanocytes induced by an RNA–DNA oligonucleotide." *Nature Biotechnology* 1343–1346 (1998).

Giver and Arnold "Combinatorial protein design by in vitro recombination" *Current Opinion in Chemical Biology* (1998) 2:335–338.

Zhao et al., "Molecular evolution by staggered extension process (StEP) in vitro recombination" *Nature Biotechnology* vol. 16 (1998) pp. 258–261.

Crameri and Stemmer "$10^{20}$—Fold aptamer library amplification without gel purification" *Nucleic Acid Research* (1993) vol. 21, no. 18 pp. 4110.

Feng and Doolittle "Progressive Sequence Alignment as a Prerequisite to Correct Phylogenetic Trees" *J. Mol. Evol.* 35:351–360 (1987).

Higgins and Sharp "Fast and sensitive multiple sequence alignments on a microcomputer" *CABIOS* 5:151–153 (1989).

Sun "Modeling DNA Shuffling" *Journal of Computational Biology* 6(1):77–90.

Altschul et al., "Basic Local Alignment Search Tool" *J. Mol. Biol.* 215:403–410 (1990).

Boehnke et al., "Statistical Methods for Multipoint Radiation Hybrid Mapping" *Am. J. Hum. Genet.* (1987) 49:1174–1188.

Brunner and Bujard "Promoter recognition and promoter strength in the *Escherichia coli* system" *EMBO J.* 6:3139–3144.

Chang et al., "Evolution of a cytokine using DNA family shuffling" *Nature Biotechnology* (1999) 17:793–797.

Christians et al., "Directed evolution of thymidine kinase for AZT phosphorylation using DNA family shuffling" *Nature Biotechnology* (1999) 17:259–264.

Crameri and Stemmer "Combinatorial multiple cassette mutagenesis creates all the permutations of mutant and wildtype cassettes" *BioTechniques* (1995) 18:194–195.

Crameri et al., "Construction and evolution of antibody–phage libraries by DNA shuffling" *Nature Medicine* (1996) 2:100–103.

Crameri et al., "Improved Green Fluorescent Protein by Molecular Evolution Using DNA Shuffling" *Nature Biotechnology* (1996) 14:315–319.

Crameri, A. et al., (1997) "Molecular evolution of an arsenate detoxification pathway by DNA shuffling." *Nature Biotechnology* 15:436–438.

Crameri, A. et al., (1998) "DNA shuffling of a family of genes from diverse species accelerates directed evolution." *Nature* 391:288–291.

Gates, C.M. et al., (1995) "Affinity selective isolation of ligands from peptide libraries through display on a lac repressor 'headpiece dimer". *Journal of Molecular Biology* 255:373–386.

Irvine et al., "SELEXION: Systematic Evolution of Ligands by Exponential Enrichment with Integrated Optimization by Non–linear Analysis" *J. Mol. Biol.* (1991) 222:739–761.

Josson et al., "Quantitative sequence–activity models (QSAM)–tools for sequence design" *Nucleic Acids Res.* (1993) 21(3):733–739.

Kelly et al., "A Test of the Markovian Model of DNA Evolution" *Biometrics* (1994) 50(3):653–664.

Knaus and Bujard "$P_L$ of coliphage lambda: an alternative solution for an efficient promoter" *EMBO* (1998) 7(9):2919–2923.

Lander and Waterman "Genomic Mapping by Fingerprinting Random Clones: A Mathematical Analysis" *Genomics* (1988) 2:231–239.

Lanzer and Bujard "Promoters largely determine the efficiency of repressor action" *Proc. Natl. Acad. Sci.* (1988) 85:8973–8977.

Minshull and Stemmer "Protein evolution by molecular breeding" *Current opinion in Chemical Biology* (1999) 3:284–290.

Ness, J. et al., (1999) "DNA shuffling of subgenominc sequences of subtilisin." *Nature Biotechnology* 17:893–896.

Stemmer "Rapid evolution of a protein in vitro by DNA shuffling" *Nature* (1994) 370–389–391.

Stemmer (1995) "Searching Sequence Space" *Bio/Technology* 13:549–553.

Stemmer (1995) "The Evolution of Molecular Computation." *Science* 270:1510.

Stemmer (1996) "Sexual PCR and Assembly PCR." In: *The Encyclopedia of Molecular Biology*. VCH Publishers, New York. pp. 447–457.

Stemmer and Soong (1999) "Molecular Breeding of viruses for targeting and other clinical properties." *Tumor Targeting* 4:1–4.

Sun and Waterman "A Mathematical Analysis of in vitro Molecular Selection–Amplification" *J. Mol. Biol.* (1996) 258:650–660.

Patten, P.A. et al., (1997) "Application of DNA Shuffling to Pharmaceuticals and Vaccines." *Current Opinion in Biotechnology* 8:724–733.

Zhang, J. et al., "Directed evolution of an effective fucosidase from a galactosidase by DNA shuffling and screening" *Proceedings of the National Academy of Sciences, USA* (1997) 64:4504–4509.

Alberts et al. "Recombinant DNA Technology." *New York Publishing, Inc.* 291–312 (1994).

Arkin "Optimizing Nucleotide Mixtures to Encode Specific Subsets of Smino Acids for Semi–Random Mutagenesis." Biotechnology (N Y). Mar. 1992;10(3):297–300.

Arkin "An algorithm for protein engineering: Simulations of recursive ensemble mutagenesis." Proc Natl Acad Sci U S A. Aug. 15, 1992;89(16):7811–5.

Barlett "Long–lasting gene repair." *Nature Biotechnology* 16:1312 (1998).

Botstein et al. "Strategies and Applications of in Vitro Mutagenesis." *Science* 229:1193–1201 (1985).

Carter "Site–directed mutagenesis." *Biochem J.* 237:1–7 (1986).

Carter "Improved Oligonucleotide–Directed Mutagenesis Using M13 Vectors." *Methods in Enzymol* 154:382–403 (1987).

Carter "Improved oligonucleotide site–directed mutagenesis using M13 vectors." *Nucleic Acids Res.* 13:4431–4443 (1985).

Chee et al. "Accessing Genetic Information with High–Density DNA Arrays." *Science* 274:610–614 (1996).

Cole–Strauss et al. "Correction of the Mutation Responsible for Sickle Cell Anemia by an RNA–DNA Oligonucleotide." *Science* 1386–1389 (1996).

Dale et al. "Oligonucleotide–directed Random Mutagenesis Using the Phosporothioate Method." *Methods Mol. Biol.* 57:369–374 (1996).

Delagrave "Searching Sequence Space to Engineer Proteins: Exponential Ensemble Mutagenesis." Biotechnology (N Y). Dec. 1993;11(13):1548–52.

Delagrave "Recursive ensemble mutagenesis." Protein Eng. Apr. 1993;6(3):327–31.

Delagrave "Context dependence of phenotype prediction and diversity in combinatorial mutagenesis." Protein Eng. Mar. 1995;8(3):237–42.

Egea Biosciences, Inc. "Pathway to the Proteome".

Fodor et al. "Light–Directed, Spatially Addressable Parallel Chemical Synthesis." *Science* 251:767–777 (1991).

Fodor "Genome Analysis: Genome Technology." *FASEB Journal* 11:121 (1997).

Fodor "Massively Parallel Genomics." *Science* 227:393–395 (1997).

Goldman "An Algorithmically Optimized Combinatorial Library Screened by Digital Imaging Spectroscopy." Biotechnology (N Y). Dec. 1992;10(12):1557–61.

Hill et al. "The structure of granulocyte–colony–stimulating factor and its relationship to other growth factors." *PNAS* 90:5167 (1993).

Kaczorowski et al. "Co–operatively of hexamer ligation." *Gene* 179(1):189–193 (1996).

Karlin et al. "Applications and statistics for multiple high–scoring segments in molecular sequences." *PNAS USA* 90:5873–5787 (1993).

Kayushin et al. "A convenient approach to the synthesis of trinucleotide phosphoroamidites–synthons for the generation of oligonucleotide/peptide libraries." *Nucleic Acids Res.* 24:3748–3755 (1996).

Kren et al. "Targeted Nucleotide Exchange in the Alkaline Phosphates Gene of HuH–7 Cells Mediated by a Chimeric RNA/DNA Oligonucleotide." *Hepatology* 25(6):1462–1468 (1997).

Kren et al. "In Vivo site–directed mutagenesis of the factor IX gene by chimeric RNA/DNA oligonucleotides." *Nature Medicine* 4(3):285–290 (1998).

Kunkel "The Efficiency of Oligonucleotide–Directed Mutagenesis." *Nucleic Acids & Mol. Biol* (1997).

Ling et al. "Approaches to DNA Mutagenesis: An Overview." *Anal Biochem.* 254(2):157–178 (1997).

Mehling et al. "Nucleotide sequences of streptomycete 16S ribosomal DNA: towards a specific identification system for streptomycetes using PCR." *Microbiology* 141:2139–2147 (1995).

Mintz et al. "EHD1–An EH–Domain–Containing Protein with a Specific Expression Pattern." *Genomics* 59(1):66–76 (1999).

Muerhoff et al. Identification of conserved nucleotide sequences within the GB virus c 5'–untranslated region: Design of PCR primers for detection of viral RNA *J. Virological Methods* 62:55–62 (1996).

Nakamaye et al. "Inhibition of restriction endonuclease Nci I Cleavage by phoshorothioate groups and its applications to oligonucleotide–directed mutagenesis." *Nucleic Acids. Res.* 14:9679–9698 (1986).

Needleman et al. "A General Method Applicable to the Search for Similarities in the Amino Acid Sequence of Two Proteins." *J. Mol. Biol.* 48:443 (1970).

Pathy "Modular exchange principles in proteins." *Curr Opinion in Structural Biology* 1:351–361 (1991).

Pathy "Introns and exons." *Curr. Opinion in Structural Biology* 4:383–392 (1994).

Pearson et al. "Improved tools for biological sequence comparison." *PNAS* 85:2444 (1988).

Porter et al. "Direct PCR Sequencing with boronated Nucleotides." *Nucleic Acids Res.* 25(8):1611–1617 (1997).

Robles "Hydropathy and Molar Volume Constraints on Combinatorial Mutants of the Photosynthetic Reaction Center." J Mol Biol. Jul. 5, 1993;232(1):242–52.

Sayers et al. "5'–3' Exonucleases in phosphorothiote–biased oligonucleotide–directed mutagenesis." *Nucleic Acids Res.* 16:791–802(1988).

Sayers et al. "Strand specific cleavage of phosphorothioate–containing DNA by reaction with restriction endonucleases in the presence of ethidium bromide." *Nucleic Acids Res.* 16:803–814 (1988).

Singh et al. "Application of Genetic Algorithms to Combinatorial Synthesis: A Computational Approach to Lead Identification and Lead Optimization." *J. Chem Inf. Comput. Sci* 118:1669–1679 (1996).

Smith "In Vitro Mutagenesis." *Ann. Rev. Genet.* 19:423–462 (1985).

Smith et al. "Comparison of Biosequences." *Adv. Appl. Math* 2:482 (1981).

Strauss "The Site–Specific Correction of Genetic Defects." *Nature Medicine* 4:274–275 (1998).

Taylor et al. "The use of phosphorothioate–modified DNA in restriction enzyme reactions to prepare nicked DNA." *Nucleic Acids Res.* 13:8749–8764 (1985).

Taylor et al. "The rapid generation of oligonucleotide–directed mutations at high frequency using phosphorothioate–modified DNA." *Nucleic Acids Res.* 13:8765–8787 (1985).

Virnekas et al. "Trinucleotide phisphoramidites: ideal reagents for the synthesis of mixed oligonucleotides for random mutagenesis." *Nucleic Acids Res.* 22:5600–5607 (1994).

Von Der Osten et al. "Protein engineering of subtilisins to improve stability in detergent formulations." *J. Biotechnol.* 28:55–68 (1993).

Wells "Importance of hydrogen–bond formation in stabilizing the transition state of subtilisin." *Trans. R. Soc. Lond.* A317:415–423 (1986).

Xiang et al. "Targeted gene conversion in a mammalian CD34+–enriched cell population using a chimeric RNA/DNA oligonucleotide." *J. Mol. Med.* 75:829–835 (1997).

Yoon et al. "Targeted gene correction of episomal DNA in mammalian cells mediated by a chimeric RNA–DNA oligonucleotide." *PNAS* 93:2071–2076 (1996).

Youvan "Imaging Sequence Space." Nature. May 5, 1994;369(6475):79–80.

Zang et al. "Directed evolution of a fucosidase from a galactosidase by DNA shuffling and screening." *PNAS USA* 94:4504–4509 (1997).

Zoller "New recombinant DNA methodology for protein engineering." *Curr. Opinion in Biotechnology* 3:348–354 (1992).

Sun "Modeling DNA Shuffline." Pro. @nd. Inter. Conf Computational Molecular Biol. 251–257 (1998).

Dewey et al. (1998) "Non–equilibrum Thermodynamics of Molecular Evolution." *J. Theor Biol.*193:593–599.

Diatchenko et al. (1996) "Suppression subtractive hybridization: A method for generating different regulated or tissue–specific cDNA probes and libraries." PNAS USA 93:6025–6030.

Morchio et al. (1997) "Simulation of Protein Evolution: Evidence for a Non–linear Aminoacidic Substitution Rate." *Riv Biol* 83–94.

Shao et al. (1998) "Random–priming in vitro recombination: an effective tool for directed evolution." *Nucleic Acids Research* 26(2):681–683.

Singapore Examination Report dated Jul. 25, 2001 for SG 0004677–1 Filed Jan. 18, 2000.

Singapore Examination Report dated Jul. 27, 2001 for SG 0004561–7 Filed Jan. 18, 2000.

Chamberlain et al. (1990) "Multiplex PCR for the Diagnosis of Duchenne Muscular Dystrophy." *PCR Protocols* 272–281.

Hayashi et al. (1994) "Simultaneous Mutagenesis of Antibody CDR Regions by Overlap Extension and PCR." *BioTechniques* 17(2):310–315.

Jirholt et al. (1998) "Exploiting sequence space: shuffling in vivo formed complementarity determining regions into a master framework." *Gene* 215:471–476.

Kobayashi et al (1997) "Analysis of Assembly of Synthetic Antibody Fragments: Expression of Functional scFv with Predefined Specificity." *BioTechniques* 23(3):500–503.

Prodromou et al (1992) "Recursive PCR: a novel technique for total gene synthesis." *Protein Engineering* 5(8):827–829.

Soderlind et al.(1999) "Complementarity–determining region (CDR) implantatio: a theme or recombination." *Immunothnology* 4:279–285.

Soderlind et al.((2000) "Recombining germlineOderived CDR sequences for creating diverse single–framework antibody libraries." *Nature Biothecnology* 18:852–856.

Soderlind et al. (1995) "Domain libraries: Synthetic diversity for de novo design of antibody V–regions." *Gene* 160:269–272.

Aita et al., "Analysis of Local Fitness Landscape with a Model of the Rough Mt. Fuji–Type Landscape: Application to Prolyl Endopeptidase and Thermolysin," Biopolymers. vol. 54, pp. 64–79, Accepted Jan. 14, 2000.

Hellberg et al., "The Prediction of Bradykinin Potentiating Potency of Pentapeptides. An Example of a Peptide Quantitative Structure–Activity Relationship," Acia Chemica Scandinaviea B 40, pp. 135–140, 1988.

Bucht et al., "Optimising the Signal Peptide for Glycosyl Phosphatidylinositol Modification of Human Acetylcholenesterase Using Mutational Analysis and Peptide–Quantitative Structure–Activity Relationships," Biochimica et Biophysica Acta 1431, pp. 471–482, 1999.

Sandberg et al., "Engineering Multiple Properties of a Protein by Combinatorial Mutagenesis," Proc. Natl. Acad. Sci. USA, vol. 90, pp. 8367–8371, Sep. 1993.

Wrede et al., "Peptide Design Aided by Neural Networks: Biological Activity of Artificial Signal Peptidase I Cleavage Sites," Biochemistry, 37, pp. 3588–3593, 1998.

Jill Damborsky, "Quantitative Structure–Function and Structure–Stability Relationship of Purposely Modified Proteins," Protein Engineering, vol. 11, No. 1, pp. 21–30, 1998.

Hellberg, et al., "Peptide Quantitative Structure—Activity Relationships, a Multivariate Approach," J. Med Chem, 30: pp 1126–1195, 1987.

Sandberg et al., "New Chemical Descriptors Relevant for the Design of Biologically Active Peptides. A Multivariate Characterization of 87 Amino Acids," J. Med Chem., 41, pp. 2481–2491, 1998.

Casari et al., "A Method to Predict Functional Residues in Proteins," Nat. Struct Biol., 2, pp. 171–178, 1995.

Gogos et al., "Assignment of Enzyme Substrate Specificity by Principal Component Analysis of Aligned Protein Sequences: An Experimental Test Using DNA Glycosylase Homologs," Proteins: Structure, Function, and Genetics, 40, pp. 98–105, 2000.

Suzuki et al., "A Method for Detecting Positive Selection at Single Amino Acid Sites," Mol. Biol. Evol. 16 (10): pp. 1315–1328, 1999.

Benner et al., "Amino Acid Substitution During Functionally Constrained Divergent Evolution of Protein Sequences," Protein Engineering, vol. 7, No. 11, pp. 1323–1332, 1994.

Wu et al., "Discovering Empirically Conserved Amino Acid Substitution Groups in Databases of Protein Families," Proc. Int. Conf. Intell. Syst. Mol. Biol., 4, pp. 230–240, 1996.

Adenot et al., "Peptides Quantitative Structure–Function Relationships: An Automated Mutation Strategy to Design Peptides and Pseudopeptides from Substitution Matrices," Journal of Molecular Graphics and Modelling, 17, pp. 292–309, 1999.

Norinder et al., "A Quantitative Structure–Activity Relationship Study of Some Substance P–Related Peptides," J. Peptide Res., 49, pp. 155–162, 1997.

Sandberg, "Deciphering Sequence Data a Multivariate Approach," Ph.D Thesis, Umea: Umea University, 78 pages, 1997.

Eriksson et al., "Peptide QSAR on Substance P Analogues, Enkephalins and Bradykinins Containing L–and D–Amino Acids," Acta Chemica Scandinavica, 44, pp. 50–56, 1990.

Ufkes eta l., "Further Studies on the Structure–Activity Relationships of Bradykinin–Potentiating Peptides," European Journal of Pharmacology, 79, pp. 155–158, 1982.

Dobrynin et al., "Synthesis of Model Promoter for Gene Expression in *Escherichia coli*," Symposium Series No. 7, pp. 365–376, 1980.

Skinner et al., "Potential Use of Additivity of Mutational Effects in Simplifying Protein Engineering," Proc. Natl. Acad. Sci., vol. 93, pp. 10753–10757, 1996.

Aita et al., "Theory of Evolutionary Molecular Engineering Through Simultaneous Accumulation of Advantageous Mutations," J. Theor. Biol., 207, pp/ 543–556, 2000.

Lathrop et al., "Global Optimum Protein Threading with Gapped Alignment and Empirical Pair Score Functions," J. Mol. Biol., 255, pp. 641–665, 1996.

Hellberg et al., "A Multivariate Approach to QSAR," Ph.D. Thesis, Umea, Sweden: University of Umea: 1986.

Vector NTI Suite 7.0 User's Manual (portion) describing software believed to be available prior to Feb. 1, 2000.

* cited by examiner

Initial strings A, B, and C:

String A: A1 - A2 - A3 - A4 - A5
String B: B1 - B2 - B3 - B4 - B5
String C: C1 - C2 - C3 - C4 - C5

Select substrings

String Pools:

Pool 1: A1, B1, C1
Pool 2: A2, B2, C2
Pool 3: A3, B3, C3

Concatenate substrings

New Strings:

String A: A1 - A2 - A3 - A4 - A5
String B: B1 - B2 - B3 - B4 - B5
String C: C1 - C2 - C3 - C4 - C5

Initial sequences

Subsequences aligned
by similarity

Concatenated
subsequences

FAMILY GAGGS MODEL # 1.

SUBTILISIN BACKGROUND INFORMATION:

7 PARENTS, SERINE PROTEASES, DIVERSE

TYPE OF ALIGHMENT/SIMILARITY DATA PRESENTED:
AMINOACID SEQUENCES, LEADER PEPTIDE EXCLUDED.

Percent Similarity

|   | 1 | 2 | 3 | 4 | 5 | 6 | 7 |   |                        |
|---|---|---|---|---|---|---|---|---|------------------------|
| 1 |   | 62.1 | 81.4 | 57.6 | 81.8 | 56.1 | 59.1 | 1 | A27211 synthetic 309.PM |
| 2 | 50.5 |   | 61.0 | 54.9 | 59.5 | 58.2 | 60.8 | 2 | BACAPRQ subtilisin.PM |
| 3 | 21.0 | 52.0 |   | 54.6 | 78.4 | 50.6 | 53.2 | 3 | BACAPRS subtilisin.PM |
| 4 | 54.4 | 63.3 | 62.3 |   | 52.0 | 64.6 | 67.9 | 4 | BACSBTL subtilisin.PM |
| 5 | 20.5 | 54.9 | 25.1 | 65.6 |   | 53.9 | 56.5 | 5 | BACYAB subtilisin alk.PM |
| 6 | 58.6 | 56.6 | 72.2 | 44.2 | 63.4 |   | 94.9 | 6 | BLSC11594 subtilisin.PM |
| 7 | 52.5 | 51.4 | 66.0 | 38.5 | 57.8 | 4.9 |   | 7 | I82494 keratinase.PM |
|   | 1 | 2 | 3 | 4 | 5 | 6 | 7 |   |                        |

METHODS OF POPULATING DATA STRUCTURES FOR USE IN EVOLUTIONARY SIMULATIONS

CROSS-REFERENCE TO RELATED APPLICATIONS

This application is a continuation of "METHODS OF POPULATING DATA STRUCTURES FOR USE IN EVOLUTIONARY SIMULATIONS" by Selifonov and Stemmer, U.S. Ser. No. PCT/US00/01138, Filed Jan. 18, 2000, and is a continuation-in-part of "METHODS OF POPULATING DATA STRUCTURES FOR USE N EVOLUTIONARY SIMULATIONS" by Selifonov and Stemmer, U.S. Ser. No. 09/416,837 (now abandoned), filed Oct. 12, 1999.

This application is also a continuation-in-part of "METHODS FOR MAKING CHARACTER STRINGS, POLYNUCLEOTIDES AND POLYPEPTIDES HAVING DESIRED CHARACTERISTICS" by Selifonov et al., filed Jan. 18, 2000, U.S. Ser. No. 09/494,282, and is a continuation-in-part of "METHODS FOR MAKING CHARACTER STRINGS, POLYNUCLEOTIDES AND POLYPEPTIDES HAVING DESIRED CHARACTERISTICS" by Selifonov et al., filed Jan. 18, 2000, U.S. Ser. No. PCT/US00/1202; which are continuation-in-part applications of "METHODS FOR MAKING CHARACTER STRINGS, POLYNUCLEOTIDES AND POLYPEPTIDES HAVING DESIRED CHARACTERISTICS" by Selifonov et al., U.S. Ser. No. 09/416,375 (now abandoned), filed Oct. 12, 1999, which is a non provisional of "METHODS FOR MAKING CHARACTER STRINGS, POLYNUCLEOTIDES AND POLYPEPTIDES HAVING DESIRED CHARACTERISTICS" by Selifonov and Stemmer, U.S. Ser. No. 60/116,447, filed Jan. 19, 1999 and a non-provisional of "METHODS FOR MAKING CHARACTER STRINGS, POLYNUCLEOTIDES AND POLYPEPTIDES HAVING DESIRED CHARACTERISTICS" by Selifonov and Stemmer, U.S. Ser. No. 60/118,854, filed Feb. 5, 1999.

This application is also a continuation-in-part of "OLIGONUCLEOTIDE MEDIATED NUCLEIC ACID RECOMBINATION" by Crameri et al., filed Jan. 18, 2000, U.S. Ser. No. 09/484,850 (now U.S. Pat. No. 6,368,861) and a continuation-in-part of "OLIGONUCLEOTIDE MEDIATED NUCLEIC ACID RECOMBINATION" by Crameri et al., filed Jan. 18, 2000, U.S. Ser. No. PCT/US00/01203, which are continuation-in-part applications of "OLIGONUCLEOTIDE MEDIATED NUCLEIC ACID RECOMBINATION" by Crameri et al., U.S. Ser. No. 09/408,392 (now U.S. Pat. No. 6,376,246), filed Sep. 28, 1999, which is a non-provisional of "OLIGONUCLEOTIDE MEDIATED NUCLEIC ACID RECOMBINATION" by Crameri et al., U.S. Ser. No. 60/118,813, filed Feb. 5, 1999 and a non-provisional of "OLIGONUCLEOTIDE MEDIATED NUCLEIC ACID RECOMBINATION" by Crameri et al., U.S. Ser. No. 60/141,049, filed Jun. 24, 1999.

COPYRIGHT STATEMENT

A portion of the disclosure of this patent document contains material which is subject to copyright protection. The copyright owner has no objection to the facsimile reproduction by any one of the patent document or the patent disclosure, as it appears in the Patent and Trademark Office patent file or records, but otherwise reserves all copyright-rights whatsoever.

STATEMENT AS TO RIGHTS TO INVENTIONS MADE UNDER FEDERALLY SPONSORED RESEARCH AND DEVELOPMENT

Not Applicable

FIELD OF THE INVENTION

This invention relates to the field of computer modeling and simulations. In particular, this invention provides novel methods of populating data structures for use in evolutionary modeling.

BACKGROUND OF THE INVENTION

There is an extensive history of the use of computers to simulate and/or investigate the evolution of life, of individual genetic systems and/or population genetic/phenotypic systems. The motor propelling most artificial life (Alife) simulations is an algorithm which allows artificial creatures to evolve and/or adapt to their environment. The fundamental algorithms fall into two dominant categories: learning algorithms (e.g., algorithms typified by neural networks) and evolutionary algorithms, typified, for example, by genetic algorithms.

Many artificial life researchers, especially those concerned with higher-order processes such as learning and adaptation, endow their organisms with a neural net which serves as an artificial brain (see, e.g., Touretzky (1088–1991). *Neural Information Processing Systems*, volume 1–4. Morgan Kaufmann, 1988–1991. Neural networks are learning algorithms. They may be trained e.g. to classify images into categories. A typical task is to recognize to which letter a given hand-written character corresponds.

A neural net is composed of a collection of input-output devices, called neurons, which are organized in a (highly connected) network. Normally the network is organized into layers: an input layer which receives sensory input, any number of so-called hidden layers which perform the actual computations, and an output layer which reports the results of these computations. Training a neural network involves adjusting the strengths of the connections between the neurons in the net.

The other major type of biologically inspired fundamental algorithms are the evolutionary algorithms. While learning processes (e.g., neural networks) are metaphorically based on learning processes in individual organisms, evolutionary algorithms are inspired by evolutionary change in populations of individuals. Relative to neural nets, evolutionary algorithms have only recently gained wide acceptance in academic and industrial circles.

Evolutionary algorithms are generally iterative. An iteration is typically referred to as a "generation". The basic evolutionary algorithm traditionally begins with a population of randomly chosen individuals. In each generation, the individuals "compete" among themselves to solve a posed problem. Individuals which perform relatively well are more likely to "survive" to the next generation. Those surviving to the next generation may be subject to a small, random modifications. If the algorithm is correctly set up, and the problem is indeed one subject to solution in this manner, then as the iteration proceeds the population will contain solutions of increasing quality.

The most popular evolutionary algorithm is the genetic algorithm of J. Holland (J. H. Holland (1992) *Adaptation in Natural and Artificial Systems*. University of Michigan Press 1975, Reprinted by MIT Press.). The genetic algorithm is widely used in practical contexts (e.g., financial forecasting, management science, etc.). It is particularly well-adapted to multivariate problems whose solution space is discontinuous ("rugged") and poorly understood. To apply the genetic algorithm, one defines 1) a mapping from the set of parameter values into the set of (0–1) bit strings (e.g. character strings), and 2) a mapping from bit strings into the reals, the so-called fitness function.

In most evolutionary algorithms, a set of randomly-chosen bit strings constitutes the initial population. In the basic genetic algorithm, a cycle is repeated during which: the fitness of each individual in the population is evaluated; copies of individuals are made in proportion to their fitness; and the cycle is repeated. The typical starting point for such evolutionary algorithms is a set of randomly chosen bit strings. The use of an "arbitrary", random or haphazard starting population can strongly bias the evolutionary algorithm away from an efficient, accurate or concise solution to the problem at hand, particularly where the algorithm is used to model or analyze a biological history or process. Indeed, the only "force" driving the evolutionary algorithm to any solution whatsoever is a fitness determination and associated selection pressure. While a solution may eventually be reached, because the process starts from a random (e.g. arbitrary) initial state in which the population members bear no relationship to each other, the population dynamics as the algorithm proceeds reveals little or no information reflecting the dynamics of the simulated system.

In addition, evolutionary algorithms are typically relatively high order simulations and provide population level information. Specific genetic information, if it is present at all, typically exists as an abstract representation of an allele (typically as a single character) or allele frequency. Consequently evolutionary algorithms provide little or no information regarding events on a molecular level.

Similarly, neural nets and/or cellular automata, take as their starting point, essentially artificial constructs and utilize internal rules (algorithms) to approximate biological processes. As a consequence such models generally mimic processes or metaprocesses, but again afford little or no information or insight regarding events at the molecular level.

SUMMARY OF THE INVENTION

This invention provides novel methods of generating "initial" populations suitable for further computational manipulation, e.g. via genetic/evolutionary algorithms. The members of populations generated by the methods of this invention possess varying degrees of "relatedness" or "similarity" to each other reflective of the degrees of covariance found in naturally occurring populations. In addition, unlike the populations used as input in typical evolutionary algorithms, the populations generated by the methods provided herein typically contain detailed information about individual members and the information is typically of sufficient complexity to provide a "continuous" (rather than binary) measure of intermember variability and/or relatedness. Indeed the methods of this invention provide detailed coding of molecular information in the individuals comprising the populations created according to the methods of this invention.

Thus, in one embodiment, this invention provides methods of populating a data structure with (e.g. generating a collection or library of) character strings. The method preferably involve i) encoding two or more a biological molecules into character strings to provide a collection of two or more different initial character strings wherein each of said biological molecules comprises at least about 10 subunits; ii) selecting at least two substrings from said character strings; iii) concatenating said substrings to form one or more product strings about the same length as one or more of the initial character strings; iv) adding the product strings to a collection of strings (a datastructure); and v) optionally repeating steps (i) or (ii) through (iv) using one or more of said product strings as an initial string in the collection of initial character strings. In particularly preferred embodiments, the "encoding" comprises encoding one or more nucleic acid sequences and/or one or more amino acid sequences into the character strings. The nucleic acid and/or amino acid sequences can be unknown and/or haphazardly selected, but preferably encode known protein(s). In one preferred embodiment, biological molecules are selected such that they have at least about 30%, preferably at least about 50%, more preferably at least about 75%, and most preferably at least about 85%, 90%, or even 95% sequence identity with each other.

In one embodiment, the substring(s) are selected such that the ends of the substrings occur in character string regions of about 3 to about 300, preferably about 6 to about 20, more preferably about 10 to about 100 and most preferably about 20 to about 50 characters that have higher sequence identity with the corresponding region of another of the initial character strings than the overall sequence identity between the same two strings. In another embodiment, the selecting can involve selecting substrings such that the ends of said substrings occur in predefined motifs of about 4 to about 100, preferably from about 4 to about 50, even more preferably from about 4 to about 10, still more preferably from about 6 to about 30 and most preferably from about 6 to about 20 characters.

In one embodiment, the selecting and concatenating can compromise concatenating substrings from two different initial strings such that the concatenation occurs in a region of about three to about twenty characters having higher sequence identity between two different initial strings than the overall sequence identity between the two different initial strings. The selecting can also comprise aligning two or more of said initial character strings to maximize pairwise identity between two or more substrings of the character strings, and selecting a character that is a member of an aligned pair for the end of one substring.

In certain embodiments, the "adding" step involves calculating the theoretical PI, PK, molecular weight, hydrophobicity, secondary structure and/or other properties of a protein encoded by the character string. In one preferred embodiment, the product strings are added to the collection (datastructure) only if they have greater than 30%, preferably greater than 50%, more preferably greater than 75% or 85% sequence identity with the initial strings.

The method can further involve randomly altering one or more characters of the character strings. This can be accomplished according to a number of methods including, but not limited to introducing a random string into the initial string collection and/or utilizing a stochastic operator as described herein. In a particularly preferred embodiment, the operations described above are performed in a computer.

In another embodiment, this invention provides a computer program product comprising computer code that i) encodes two or more a biological molecules into character strings to provide a collection of two or more different initial character strings wherein each of said biological molecules comprises at least about ten subunits; ii) selects at least two substrings from the character strings; iii) concatenates the substrings to form one or more product strings about the same length as one or more of the initial character strings; iv) adds the product strings to a collection of strings (i.e., populates a datastructure); and v) optionally repeats steps (i) or (ii) through (iv) using one or more of the product strings as an initial string in the collection of initial character strings. In other words, the computer program product comprising computer code that performs the operations described herein. The program code can be provided in compiled form, as source code, as object code, as an executable, etc. The program can be provided on any convenient medium, e.g., magnetic media, optical media, electronic media, optomagnetic media, etc. The code can also be present on a computer, e.g. in memory (dynamic or static memory) on a hard drive, etc.

In another embodiment, this invention provides a system for generating labels (tags) and/or music derived from the sequences of biological molecules. The system comprises an encoder for encoding two or more initial strings from biological molecules (e.g. nucleic acid and/or proteins); an isolator for identifying and selecting substrings from the two or more strings; a concatenator for concatenating the substrings; a data structure for storing the concatenated substrings as a collection of strings; a comparator for measuring the number and/or variability of the collection of strings and determining that sufficient strings exist in the collection of strings; and a command writer for writing the collection of strings into a raw string file. In a preferred embodiment, the isolator comprises a comparator for aligning and determining regions of identity between two or more initial strings. Similarly the comparator may comprise a means for calculating sequence identity and the isolator and comparator may optionally share this means. In preferred embodiments, the isolator selects substrings such that the ends of said substrings occur in string regions of about three to about 100 characters that have higher sequence identity with the corresponding region of another of the initial character strings than the overall sequence identity between the same two strings.

In another embodiment, the isolator selects substrings such that the ends of said substrings occur in predefined motifs of about 4 to about 100, preferably from about 4 to about 50, even more preferably from about 4 to about 10, still more preferably from about 6 to about 30 and most preferably from about 6 to about 20 characters. In one embodiment, the isolator and concatenator individually or in combination concatenate substrings from two different initial strings such that the concatenation occurs in a region of about 3 to about 300, more preferably about 5 to about 200, most preferably from about 10 to about 100 characters having higher sequence identity between said two different initial strings than the overall sequence identity between said two different initial strings. In one preferred implementation, the isolator aligns two or more of the initial character strings to maximize pairwise identity between two or more substrings of the character strings, and selects a character that is a member of an aligned pair for the end of one substring.

The comparator can impose any of a wide variety of selection criteria. Thus, in various embodiments, the comparator can calculate theoretical PI, PK, molecular weight, hydrophobicity, secondary structure and/or other properties of an encoded protein. In one preferred embodiment, the comparator adds strings to the data structure only if they have greater than 30% identity with the initial strings.

The system can, optionally, comprising an operator that randomly alters one or more characters of the character strings. In certain embodiments, such an operator can randomly select and alter one or more occurrences of a particular preselected character in said character strings. Preferred datastructures in this system stores encoded (or deconvolved) nucleic acid sequences and/or encoded or deconvolved amino acid sequences.

A further understanding of the invention can be had from the detailed discussion of specific embodiments below. For purposes of clarity, this discussion refers to devices, methods, and concepts in terms of specific examples. However, the method of the present invention may operate within a variety of types of logical devices. It is therefore intended that the invention not be limited except as provided in the attached claims (as interpreted under the doctrine of equivalents).

Furthermore, it is recognized that logic systems can include a wide variety of different components and different functions in a modular fashion. Different embodiments of a system can include different mixtures of elements and functions and may group various functions as parts of various elements. For purposes of clarity, the invention is described in terms of systems that include many different innovative components and innovative combinations of components. No inference should be taken to limit the invention to combinations containing all of the innovative components listed in any illustrative embodiment in this specification.

Definitions

The terms "character string" "word", "binary string" or "encoded string" represent any entity capable of storing sequence information (e.g. the subunit structure of a biological molecule such as the nucleotide sequence of a nucleic acid, the amino acid sequence of a protein, the sugar sequence of a polysaccharide, etc.). In one embodiment, the character string can be a simple sequence of characters (letters, numbers, or other symbols) or it can be numeric representation of such information in tangible or intangible (e.g. electronic, magnetic, etc.) form. The character string need not be "linear", but can also exist in a number of other forms, e.g. a linked list, etc.

A "character" when used in reference to a character of a character string refers to a subunit of the string. In a preferred embodiment, the character of a character string encodes one subunit of the encoded biological molecule. Thus, for example, in a preferred embodiment, where the encoded biological molecule is a protein, a character of the string encodes a single amino acid.

A "motif" refers to a pattern of subunits comprising a biological molecule. The motif can refer to a subunit pattern of the unencoded biological molecule or to a subunit pattern of an encoded representation of a biological molecule.

The term substring refers to a string that is found within another string. The substring can include the full length "parent" string, but typically, the substring represents a substring of the full-length string.

The term "data structure" refers to the organization and optionally associated device for the storage of information, typically multiple "pieces" of information. The data structure can be a simple recordation of the information (e.g., a list) or the data structure can contain additional information (e.g., annotations) regarding the information contained therein, can establish relationships between the various "members" (information "pieces") of the data structure, and can provide pointers or linked to resources external to the data structure. The data structure can be intangible but is rendered tangible when stored/represented in tangible medium. The data structure can represent various information architectures including, but not limited to simple lists, linked lists, indexed lists, data tables, indexes, hash indices, flat file databases, relational databases, local databases, distributed databases, thin client databases, and the like. In preferred embodiments, the data structure provides fields sufficient for the storage of one or more character strings. The data structure is preferably organized to permit alignment of the character strings and, optionally, to store information regarding the alignment and/or string similarities and/or string differences. In one embodiment this information is in the form of alignment "scores" (e.g., similarity indices) and/or alignment maps showing individual subunit (e.g., nucleotide in the case of nucleic acid) alignments. The term "encoded character string" refers to a representation of a biological molecule that preserves desired sequence/ structural information regarding that molecule.

Similarity, when used herein can refer to a similarity measurement between the encoded representation(s) of a molecule (e.g., the initial character strings) or between the molecules represented by the encoded character strings.

When referring to operations on strings (e.g. insertions, deletions, transformations, etc.) it will be appreciated that the operation can be performed on the encoded representation of a biological molecule or on the "molecule" prior to encoding so that the encoded representation captures the operation.

The term "subunit" when used in reference to a biological molecule refers to the characteristic "monomer" of which a biological is composed. Thus, for example, the subunit of a nucleic acid is a nucleotide, the subunit of a polypeptide is an amino acid, the subunit of a polysaccharide is a sugar, etc.

The terms "pool" or "collection" are used interchangeably when used to refer to strings.

A "biological molecule" refers to a molecule typically found in a biological organism. Preferred biological molecules include biological macromolecules that are typically polymeric in nature being composed of multiple subunits. Typical biological molecules include, but are not limited to nucleic acids (formed of nucleotide subunits) proteins (formed of amino acid subunits), polysaccharides (formed of sugar subunits), etc.

The phrase "encoding a biological molecule" refers to the generation of a representation of that biological molecule that preferably contains and can therefore be used to recreate the information content of the original biological molecule.

The term "nucleic acid" refers to a deoxyribonucleotide or ribonucleotide polymer in either single- or double-stranded form, and unless otherwise limited, encompasses known analogs of natural nucleotides that can function in a similar manner as naturally occurring nucleotides.

A "nucleic acid sequence" refers to the order and identity of the nucleotides comprising a nucleic acid.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

A "polypeptide sequence" refers to the order and identity of the amino acids comprising a polypeptide.

The phrase "adding the product strings to a collection of strings" as used herein does not require a mathematical addition. Rather it refers to a process of identifying one or more strings as included within a set of strings. This can be accomplished by a variety of means including, but not limited to copying or moving the string(s) in question into a data structure that is a collection of strings, setting or providing a pointer from the string to a data structure that represents a collection of strings, setting a flag associated with the string indicating its inclusion in a particular set, or simply designating a rule that the string(s) so produced are included in the collection.

DETAILED DESCRIPTION

Figure 1:
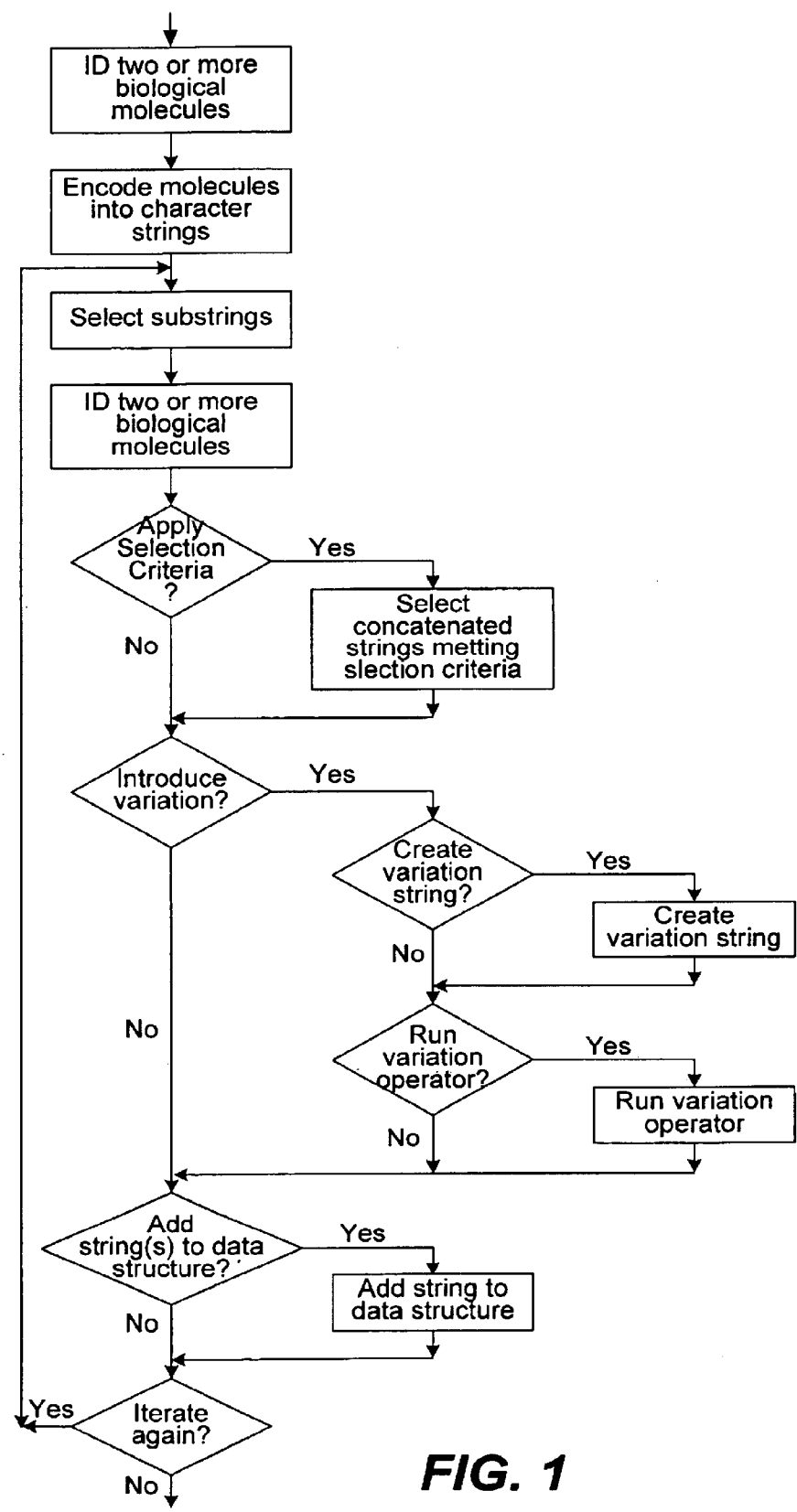
FIG. 1 illustrates a flow chart depicting one embodiment of the methods of this invention.

I. Generating Populations of Character Strings.

This invention provides novel computational methods to generate representations of actual or theoretical populations of entities suitable for use as initial (or mature/processed) populations in evolutionary models more preferably in evolutionary models typified by genetic algorithms. When initialized to reflect features of particular biological organisms, the entities generated by the methods of this invention each contain significant information regarding underlying molecular biology (e.g. representative amino acid or nucleic acid sequence(s)) and thereby permit models based on genetic or other algorithms to provide unprecedented level so information regarding evolutionary processes at the molecular level.

In particularly preferred embodiments, the methods of this invention generate populations of character strings where each character string represents one or more biological molecules. Using only a few strings as "seeds" the methods generate large populations of strings bearing an "evolutionary" relationship to the initial seed members. In contrast to traditional genetic algorithms in which initial member sets are arbitrary, random/haphazard, or selected for mathematical or representational convenience, the populations generated by the methods of this invention are, in preferred embodiments, derived from known existing biological "precursors" (e.g., particular nucleic acid sequences and/or polypeptide sequences).

In a preferred embodiment, the methods of this invention involve:

1) Identifying/selecting two or more biological molecules;
2) Encoding the biological molecules into character strings;
3) Selecting at least two substrings from the character strings;
4) Concatenating said substrings to form one or more product strings about the same length as one or more of the initial character strings;
5) Adding the product strings to a collection of strings which can be the set of initial strings or a separate set; and 6) Optionally introducing additional variation into the a resulting string set;
7) Optionally adding selection pressure to the resulting string set.
8) Optionally repeating steps (2) or (3) through (7) using one or more of the product strings as an initial string in the collection of initial character strings.

Each of these operations is described in more detail below.

II. Encoding One or More Biological Molecules into Character Strings.

The methods of this invention typically utilize one or more "seed" members. The "seed" members are preferably representations of one or more biological molecules. Thus, the initial steps of preferred embodiments of this invention involve selecting two or more biological molecules and encoding the biological molecules into one or more character strings.

A Identifying/Selecting "Seed/Initial" Biological Molecule(s).

Virtually any biological molecule can be used in the methods of this invention. However, preferred biological molecules are "polymeric" biological macromolecules comprising a multiplicity of "subunits". Biological macromolecules particularly well suited to the methods of this invention include, but are not limited to nucleic acids (e.g. DNA, RNA, etc.), proteins, glycoproteins, carbohydrates, polysaccharides, certain fatty acids, and the like.

When nucleic acids are selected, the nucleic acid can be single stranded or double stranded, although it will be appreciated that a single strand is sufficient to represent/encode a double stranded nucleic acid. The nucleic acids are preferably known nucleic acids. Such nucleic acid sequences can be readily determined from a number of sources including, but not limited to public databases (e.g., GenBank), proprietary databases (e.g. Incyte databases), scientific publications, commercial or private sequencing laboratories, in-house sequencing laboratories, etc.

The nucleic acids can include genomic nucleic acids, cDNAs, mRNAs, artificial sequences, natural sequences having modified nucleotides, and the like.

In one preferred embodiment, the two or more biological molecules are "related", but not identical. Thus, the nucleic acids may represent the same gene or genes but differ in the strain, species, genus, family, order, phylum or kingdom from which they are derived. Similarly, in one embodiment, the protein, polysaccharide, or other molecule(s) are the same protein, polysaccharide, or other molecule(s) with differences between the molecules resulting from the fact that they are selected from different strains, species, genus, families, orders, phyla or kingdoms.

The biological molecules can represent a single gene product (e.g. an MRNA, a cDNA, a protein, etc.) or they can represent a collection of gene products and/or non-coding nucleic acids. In certain preferred embodiments, the biological molecules will represent members of one or more particular metabolic pathways (e.g. regulatory, signaling or synthetic pathways). Thus, for example, the biological molecules can include members comprising an entire operon, or a complete biosynthetic pathway (e.g., the lac operon, Protein: B-DNA gal operon, the colicin A operon, the lux operon, polyketide synthesis pathways, etc.).

In certain preferred embodiments, the biological molecules can include any number of different, genes, proteins, etc. Thus, in certain embodiments, the biological molecules could include the total nucleic acid (e.g. genomic DNA, cDNA, or MRNA) or total protein, or total lipid, etc., of an individual, or multiple individuals of the same or different species.

In certain embodiments, the biological molecules can reflect a "representation" of the total population of that species' molecules. High order representation of populations of molecules is accomplished in the laboratory and, according to the methods of this invention can be performed in silico. Methods of representing complex molecules or populations of molecules are seen in Representational Difference Analysis (RDA) and related techniques (see, e.g., Lisitsyn (1995) Trends Genet., 11(8): 303–307, Risinger et al. (1994) Mol Carcinog. 11(1): 13–18, and Michiels et al. (1998) Nucleic Acids Res. 26: 15 3608–3610, and references cited therein).

Particular preferred biological molecules for encoding and manipulation in the methods of this invention include proteins and/or the nucleic acids encoding the proteins of various classes of molecules such as therapeutic proteins such as erythropoietin (EPO), insulin, peptide hormones such as human growth hormone; growth factors and cytokines such as Neutrophil activating peptide-78, GROα/MGSA, Groβ, GROγ, MIP-1α, MIP-16, MCP-1, epidermal growth factor, fibroblast growth factor, hepatocyhte growth factor, insulin-like growth factor, the interferons, the interleukins, keratinocyte growth factor, leukemia inhibitory factor, oncostatin M, PD-ECSF, PDGF, pleiotropin, SCF, c-kit ligand, angiogenesis factors (e.g. vascular endothelial growth factors VEGF-A, VEGF-B, VEGF-C, VEGF-D, placental growth factor (PLGF), etc.), growth factors (e.g. G-CSF, GM-CSF), soluble receptors (e.g. IL4R, IL-13R, IL-10R, soluble T-cell receptors, etc.), and the like.

Other preferred molecules of encoding include, but are not limited to transcription and expression activators. The transcription and expression activators include genes and/or proteins that modulate cell growth, differentiation, regulation and the like an are found in prokaryotes viruses, and eukaryotes including fungi, plants and animals. Expression activators include, but are not limited to cytokines, inflammatory molecules, growth factors, growth factor receptors, and oncogene products, interleukins (e.g., IL-1, IL2, IL-8, etc.) interferons, FGF, IGF-I, IGF-II, FF, PDGF, TNF, TGF-α, TGF-β, EGK, KGF, SCR/c-kit, CD40L/CD40, VLA-4VCAM-1, ICAM-1/LFA-1, and hyalurin/CD44, signal transduction molecules and corresponding oncogene products, e.g., Mos, RAS, Raf, and Met; and transcriptional activators and supressors, e.g., p53, Tat, Fos, Myc, Jun, Myb, Rel, and steroid hormone receptors such as those for estrogen, progesterone, testosterone, aldosterone, the LDL receptor ligand and corticosterone.

Preferred molecules for encoding in the methods of this invention also include proteins from infectious or otherwise pathogenic organisms e.g. proteins characteristic of *Aspergillus* sp., *Candida* sp., *E. coli, Staphyloccoi* sp, *Streptocci* sp., *Clostridia* sp., *Neisseria* sp., *Enterobacteriacea* sp., *Helicobacter* sp., *Vibrio* sp., *Capylobacter* sp., *Pseudomonas* sp., *Ureaplasma* Sp., *Legionella* sp., *Spirochetes, Mycobacteria* sp., *Actnomyces* sp., *Nocardia* sp., *Chlamydia* sp., *Rickettsia* sp., *Coxiella* sp., *Ehrilichia* sp., *Rochalimaea, Brucella, Yersinia, Fracisella,* and *Pasturella;* protozoa, viruses (+)RNA viruses, (−)RNA viruses, Orthomyxoviruses, dsDNA viruses, retroviues, etc.

Still other suitable molecules include nucleic acid and/or proteins that act as inhibitors of transcription, toxins of crop pests, industrially important enzymes (e.g. proteases, nucleases, and lipases) etc.

Preferred molecules include members of related "families" of nucleic acids or their encoded proteins. Relatedness (e.g. inclusion or exclusion from the "family") can be determined by protein function and/or by sequence identity with other members of the family. Sequence identity can be determined as described herein and preferred family members share at least about 30% sequence identity, more preferably at least about 50% sequence identity and most preferably at least about 80% sequence identity. In certain instances, it is desirable to include molecules that have low (e.g. less than about 30%) sequence identity), but significant relatedness. Such methods are well known in the bioinformatics literature and typically involve incorporation of molecular folding patterns with sequence/similarity information. One common implementation of such an approach includes "threading algorithms". Threading algorithms detect remote homology by comparing sequences to structural templates. If the structural similarity between target and template is sufficiently large, their relationship can be detected in the absence of significant sequence similarity. Threading algorithms are well known to those of skill in the art and can be found, for example, in the NCBI Structure Group Threading Package (available from the National Center for Biological Information and in SeqFold (Molecular Simulations, Inc.).

B) Encoding the Biological Molecule into a Character String.

The biological molecule(s) are encoded into character strings. In the simplest instance, the character string is identical to the character code used to represent the biological molecule. Thus, for example, the character string can comprise the characters A, C, G, T, or U where a nucleic acid is encoded. Similarly, the standard amino acid nomenclature can be used to represent a polypeptide sequence. Alternatively, it will be realized that, to some extent, the encoding scheme is arbitrary. Thus, for example, in the case of nucleic acids the A, C, G, T, or U can be represented by the integers 1, 2, 3, 4, and 5, respectively and the nucleic acid can be represented as a string of these integers which is itself a single (albeit typically large) integer. Other coding schemes are also possible. For example, the biological molecule can be encoded into a character string where each "subunit" of the molecule is encoded into multi-character representation. Alternatively various compressed representations are also possible (e.g., where recurrent motifs are represented only once with appropriate pointers identifying each occurrence).

The biological molecules also need not be encoded into data structures that are discrete/single strings. More complicated data structures (e.g. arrays, linked lists, indexed structures including, but not limited to databases or data tables, etc.) can also be used to encode the biological molecule(s).

Essentially any data structure capable that permits input, storage, and retrieval of a representation of the biological molecule(s) is suitable. While these operations can be accomplished manually (e.g. with pencil and paper or cardfile, etc.), preferred data structures are data structures that can be manipulated optically and/or electronically and/or magnetically and thus permit automated input, storage and output operations (e.g., by a computer).

III. Selecting Substrings.

In a preferred embodiment, the character string encoded biological molecules provide an initial population of strings from which substrings are selected. Typically at least two substrings are selected with one substring coming from each initial character string. Where there are more than two initial character strings, it is not necessary that every initial character string provide a substring as long as at least two initial character strings provide such substrings. In preferred embodiments, however, at least one substring will be selected from each initial string.

A) Substring Length.

There is essentially no limit on the maximum number of substrings that can be selected from the initial strings other than the theoretical maximum number of strings that can be generated from any given string. Thus, for example, the maximum number of substrings selected from an initial string is the number of strings generated by a complete permutation of the initial string(s).

With an initial string of relatively modest length, however, the number of permutations is quite high. Thus, in preferred embodiments, the substrings are selected from an initial string such that the substrings do not overlap. Expressed another way, in a preferred embodiment, the substrings from any one initial string are selected such that those substrings, if ligated in the correct order, would reproduce the complete initial string from which they are selected.

Preferred substrings are also selected so as to not be unduly short. Typically a substring will be no shorter than the minimum string length necessary to represent one subunit of the encoded biological molecule. Thus, for example, where the encoded biological molecule is a nucleic acid the substring will be long enough to at least encode one nucleotide. Similarly, where the encoded biological molecule is a polypeptide the substring will be long enough to at least encode one amino acid.

In preferred embodiments, the selected substring encodes at least two, preferably at least 4, more preferably at least 10, still more preferably at least 20, and most preferably at least 50, 100, 500, or 1000 subunits of the encoded biological molecule.

Substring length can be chosen to capture a particular level of biological organization. For example, a substring can be selected that encodes an entire gene, cDNA, mRNA. At a "higher" level of organization, a substring can be selected that encodes a series of related genes cDNAs, mRNAs, etc. as might be found in an operon, or a regulatory or synthetic pathway. At a still "higher" level of organization, the substring can be selected that encodes the total nucleic acid (e.g. genomic DNA, total mRNA, total cDNA) of an individual. There is essentially no limit to the "level of organization" that is captured in the substring(s) as long as the initial string from which the substring is selected encodes a higher level of organization. Thus, where the substring(s) are selected to encode individual genes, the initial string may encode entire metabolic pathways. Where the substring is selected to encode an individual's total nucleic acid, the initial string may encode the total nucleic acid of a population, etc.

Conversely, the substring can also be selected to encode a subunit of a particular level of biological organization. Thus, for example, a substring can be used to select a particular domain of a protein, a particular region of a chromosome (e.g., a region characteristically amplified, deleted or translocated), etc.

B) Substring Selection Algorithms.

Any of a wide variety of approaches can be used to selected the substring(s), the particular approach being determined by the problem that is being modeled. Preferred selection approaches include, but are not limited to random substring selection, uniform substring selection, motif-based selection, alignment-based selection, and frequency-biased selection. The same substring selection method need not be applied to every initial character string, but rather different substring selection methods can be used for different initial strings. In addition, it is possible to apply multiple substring selection methods to any initial character string.

1. Random Substring Selection.

In one simple approach, the substring(s) can be selected randomly. Many approaches are available for the "random" selection of substrings. For example, where a substring(s) of minimum length "L" are to be selected from an encoded character string of length "M", "cleavage points" can be selected using a random number generator producing integers (indicating position along the string) ranging from L to M-L (to avoid short terminal strings). "Internal" substrings of length less than L are discarded.

In another approach each position along the character string is addressed (e.g. by an integer ranging from 1 to N where N is the length of the character string). A minimum substring length "L" and a maximum substring length "M" are selected. Then a random number generator is used to generate a number "V" ranging from L to M. The algorithm then selects a substring from position 1 to V and position V+1 become position 1 again. The process is then repeated until the initial string is spanned.

Other methods of randomly selecting substrings are readily devised. For the purpose of this invention, "random" selection does not require that the selection process meet formal statistical requirements for randomness. Pseudorandom or haphazard selection is sufficient in this context.

2. Uniform Substring Selection.

In uniform substring selection, the desired number of substrings to be obtained from each initial string is determined. The initial string is then uniformly divided into the desired number of substrings. Where the initial string length does not permit uniform division one or more shorter or longer substrings may be permitted.

3. Motif-based Selection

Substrings can be selected from the initial strings using motif-based selection. In this approach, the initial character string(s) are scanned for the occurrence of particular preselected motifs. The substring is then selected such that the endpoint(s) of the substring occur in a predefined relationship to the motif. Thus, for example, the end can be within motif or "upstream" or "downstream" a preselected number of subunits from the end of the motif.

The motif can be completely arbitrary or it can reflect the properties of a physical agent or biological molecule. Thus, for example, where the encoded biological molecule is a nucleic acid, the motif can be selected to reflect the binding specificity of a restriction endonuclease (e.g., EcoRv, HindIII, BamHI, PvuII, etc.), a protein binding site, a particular intron/exon junction, a transposon, and the like. Similarly where the encoded biological molecule is a protein, the motif can reflect a protease binding site, a protein binding site, a receptor binding site, a particular ligand, a complementarity determining region, an epitope, etc.

Similarly, polysaccharides are can contain particular sugar motifs, glycoproteins can have particular sugar motifs and/or particular amino acid motifs, etc.

Motifs need not specifically reflect primary structure of the encoded biological molecule. Secondary and tertiary structure motifs are also possible and can be used to delineate substring endpoints. Thus, for example, an encoded protein may contain a characteristic α-helix, β-sheet, α-helix, motif and the occurrence of this motif can be used to delineate substring endpoints.

Another "higher order" kind of motif can a "meta-motif" e.g., as represented by a "fragmentation digest." In this approach, a substring endpoint is not determined by the occurrence of a single motif, but is delineated by coordinated pattern and spacing of one or more motifs.

Motifs can also be selected/utilized that do not strictly reflect sequence patterns, but rather the information content of particular domains of the character strings. Thus, for example, U.S. Pat. No. 5,867,402 describes a computer system and computation method for processing sequence signals by a transformation into an information content weight matrix, as represented by $R_i(b,l)$. A second transformation follows which applies a particular sequence signal to the information content weight matrix, $R_i(b,l)$ thereby producing a value, $R_i$, which comprises the individual information content of a particular sequence signal. Other approaches to the determination of information content of character strings are also known (see also Staden, (1984) Nucleic Acids Res. 12: 505–519; Schneider (1994) Nanotechnology 5: 1–8; Herman et al. (1992) J. Bacteriol. pp. 3558–3560; Schneider et al. (1990) Nucleic Acids Res., 18(20): 6097–6100; Berg, et al. (1988) J. Mol. Biol., 200(4): 709–723).

Other motifs that are contemplated reflect biological signals. Thus, for example, one motif delineating the end of a substring might be a stop codon, or a start codon in the case of an encoded nucleic acid, a methionine, or a polyadenylation signal in the case of a protein, etc.

The same motif need not be applied to every initial sequence. In addition, multiple motifs, meta-motifs and/or motif/meta-motif combinations can be applied to any sequence.

4. Alignment-based Selection.

In another approach substrings are selected by aligning two or more initial character strings and choosing regions of high identity between the initial strings in which to select the endpoints of the substring(s). Thus, for example, after a sequence alignment, substrings may be chosen such that the endpoint of the substring(s) occurs within (e.g., in the middle of) a region having at least 30%, preferably at least 50%, more preferably at least 70%, still more preferably at least 80%, and most preferably at least 85%, 90%, 95%, or even at least 99% sequence identity over a window ranging in length from at least about 5, preferably from at least about 10, more preferably from at least about 20, still more preferably from at least about 30, and most preferably from at least about 50, 100, 200, 500., or even 1000 subunits.

The terms "sequence identity" or "percent sequence identity" or "percent identity," or percent "homology" in the context of two or more biological macromolecules (e.g. nucleic acids or polypeptides), refer to two or more sequences or subsequences that are the same or have a specified percentage of subunits (e.g., amino acid residues or nucleotides) that are the same, when compared and aligned for maximum correspondence, as measured using one a sequence comparison algorithms or by visual inspection.

For sequence comparison, typically one sequence acts as a reference sequence, to which test sequences are compared. In a preferred embodiment, when using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Alignment and sequence comparison algorithms are well known to those of skill in the art. For example, optimal alignment of sequences for comparison can be algorithms including, but not limited to the local homology algorithm of Smith & Waterman (1981) Adv. Apple. Math. 2:482, the homology alignment algorithm of Needle man & Wench (1970) *J. Mol. Biol.* 48:443, by the search for similarity method of Pearson & Lipan (1988) *Proc. Natl. Acad. Sic. USA* 85:2444, by computerized implementations of these algorithms (e.g., GAP, BESTFIT, FASTA, and TFASTA) in commercial modules and/or commercial software packages (e.g., the Wisconsin Genetics Software Package, Genetics Computer Group, 575 Science Dr., Madison, Wis.), or by visual inspection (see generally Amusable et al., supra).

One example of a useful algorithm is PILEUP. PILEUP creates a multiple sequence alignment from a group of related sequences using progressive, pairwise alignments to show relationship and percent sequence identity. It also plots a tree or endogamy showing the clustering relationships used to create the alignment. PILEUP uses a simplification of the progressive alignment method of Feng & Doolittle (1987) *J. Mol. Evol.* 35:351–360. The method used is similar to the method described by Higgins & Sharp (1989) *CABIOS* 5:151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) *J. Mol. Biol.* 215:403–410. Software for performing BLAST analyses is publicly available through the National Center for Biotechnology Information [(http://www.nebi.nlm.nih.gov/)]. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et at, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff (1989) *Proc. Natl. Acad. Sci. USA* 89:10915) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g. Karlin & Altschul (1993) *Proc. Natl. Acad. Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

The above-identified similarity algorithms are intended to be exemplary and not limiting. It will be appreciated that similarity can be determined across the full length of the initial character strings or it can be restricted to particular subdomains.

5. Frequency-biased Selection.

In frequency-biased subsequence selection methods, the subsequences are selected such that the endpoints of the subsequence(s) occur in a particular relationship to subsequence domains that meet a particular preselected frequency criterion. For example, where it is desired to exclude encoded biological molecules that contain highly repetitive subunit patterns (e.g. in the case of a nucleic acid, a high concentration of AC repeats such as "ACACACACACAC", SEQ ID NO:1"), the subunit selection can be designed to create an endpoint prior to the occurrence of a particular repeat density of the particular subunit or motif of subunits. In this instant a repeat density is the number of occurrences of a subunit or subunit motif per character string length measured in subunit number or lengths of the subunit motif respectively.

Thus, in the example suggested above, the substring can be selected such that the substring endpoint occurs adjacent to a character string domain in which the AC motif occurs at a frequency over 0.5 (50%) over a length of at least e.g. 4 motif lengths (in this case 8 subunit lengths).

An other example, of such a selection is a substring selection based on the occurrence of a particular subunit at an occurrence of 100% over at least X subunits. Thus, for example, where the encoded biological molecule is a nucleic acid and the subunit is adenosine "A", the frequency-biased selection may set a substring endpoint at the occurrence of a polyadenylation signal (e.g., AAAAAAA). Depending on the design of the frequency-biased substring selection criterion, equivalent results may be obtained using a motif-based selection scheme as described above.

6. Other Criteria.

Numerous other criteria can be used to influence and/or determine the selection of particular substrings. Such criteria include the predicted hybrophobicity and/or PI and/or PK of the molecule encoded by the substring. Other criteria include the cross-over number the desired fragment size, the substring length distribution, and/or rational information regarding the folding of the molecule(s) encoded by the substring(s).

IV. Concatenating Substrings.

Once populations of substrings are selected from the initial strings, the substrings are concatenated to produce new strings of approximately or exactly the same length as the parent initial strings. The string concatenation can be performed according to a wide number of methods.

In one embodiment, the substrings are randomly concatenated to produce "recombined" strings. In one approach to such "random" concatenation, each substring is assigned a unique identifier (e.g., an integer or other identifier). The identifiers are then randomly selected from the pool (e.g., using a random number generator) and the subsequences corresponding to those identifiers are joined to produce a concatenated sequence. When joined subsequences are approximately or exactly the length of the starting character string(s), the process is started anew to produce another string. The process is repeated until all of the substrings are utilized. Alternatively the substrings can be selected without withdrawing them from the "substring pool" and the process is repeated until a desired number of "full-length" strings are obtained.

Figure 2:
FIG. 2 illustrates a selection and concatenation of subsequences according to the method(s) of this invention.
Figure 2:

In preferred embodiments, however, it is desired to maintain the relative order of substrings forming the concatenated strings as existed in the initial strings. This can be accomplished by any of a wide number of means. For example, each substring selected from a parent string can be "tagged" with an identifier (e.g. a pointer) identifying the position in the initial string of that substring relative to the position of the other substrings derived from that parent string. Substrings derived from corresponding positions in other initial strings are assigned similar positional identifiers. This approach is illustrated in FIG. 2 where three initial strings (designated A, B, and C) each give rise to five substrings numbered 1 through 5. Each substring can be uniquely identified (e.g., A1, A2 . . . A5, B1, B2, . . . B5, C1, C2, . . . C5) as illustrated. A concatenated string can then be produced by randomly selecting a substring from pool 1 (consisting of A1, B1, and C2), a substring from pool 2 (consisting of A2, B2, C2) and so on though pool 5. This process can be repeated until three strings are reconstructed.

In this concatenation scheme, once a substring is concatenated it is removed from the substring pool. However, the concatenation can be accomplished by "copying" the subsequence from the pool and thus utilizing it in a concatenated sequence while still retaining the substring availability for subsequent concatenations. This permits greater diversity to be generated.

Figure 3:
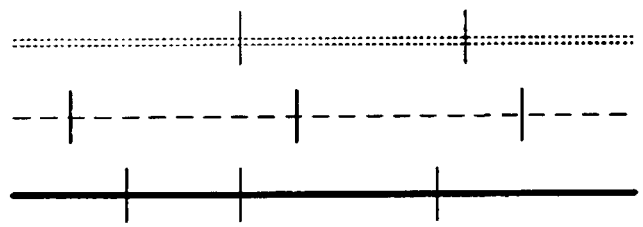
FIG. 3 illustrates a selection and concatenation of subsequences according to the method(s) of this invention where the concatenation utilizes an alignment algorithm to fix the order of substrings.
Figure 3:
Figure 3:

In other embodiments, various alignment and/or similarity algorithms can be used to generally maintain the relative sequence of the substrings during the concatenation. In this approach, subsequences are assigned a relative position in the concatenated sequence by associating regions of high similarity (see, e.g., FIG. 3).

In preferred embodiments, the initial encoded biological molecules bear some relationship with each other. Thus, for example, where the encoded molecules represent members in a particular enzyme family, molecules represent individuals from a particular population, etc. The subsequences are expected to share domains of significant similarity. In addition, critical functional domains will tend to be conserved and therefore also increase the similarity of particular domains of the subsequences. Thus, aligning regions of high similarity between subsequences will tend to reconstruct the relative order of the subsequences to reflect their order in the initial strings.

It will not require that perfect order be established in every concentrated character string. That a percentage (e.g., preferably at least 1 percent, more preferably at least 10 percent, still more preferably at least 20% and most preferably at least 40 percent, at least 60% or at least 80%) of the concatenated sequences preserve the original order is preferred.

The use of similarity measures to re-order the subsequences is similar to sequencing by hybridization (SBH) methodologies in which similarity algorithms are used to reconstruct nucleic acid sequences from fragments of the complete sequence (see, e.g.,—Baringa (1991) *Science,* 253: 1489; Bains (1992) *Bio/Technology* 10: 757–758; Drmanac and Crkvenjakov, Yugoslav Patent Application #570/87, 1987; Drmanac et al. (1989) *Genomics,* 4: 114; Strezoska et al. (1991) *Proc. Natl. Acad. Sci. USA* 88: 10089; and Drmanac and Crkvenjakov, U.S. Pat. No. 5,202,231).

It will be appreciated that certain concatenations alone, or selection and concatenation operations together can be represented by particular operators. Certain operators of this kind are known in genetics algorithms. Thus, for example, a "crossing over" (reciprocal translocation) operator can be defined in which subsequences at a similar position in two different initial sequences are exchanged. Similarly "linkage" operators can be defined that link particular subsequences in cross-over events so that the subsequences crossover together (whether or not they are adjacent subsequences). In view of the foregoing disclosure, other operators will be known to those of skill in the art.

V) Adding the Product Strings to a Collection of Strings.

The concatenated strings produced by the methods of this invention are added to a collection of strings that forms the "populated dataset". The strings in this collection can be used as initial strings in further iterations of the methods described herein (see, FIG. 1). The addition, in this context refers to a process of identifying one or more strings as included within a set of strings. This can be accomplished by a variety of means including, but not limited to copying or moving the string(s) in question into a data structure that is a collection of strings, setting or providing a pointer from the string to a data structure that represents a collection of strings, setting a flag associated with the string indicating its inclusion in a particular set, or simply designating a rule that the string(s) so produced are included in the collection.

Once one or more concatenated character strings are generated, a selection criterion can optionally be imposed to determine whether or not the concatenated strings are to be included in the collection of strings (e.g. as initial strings for a second iteration and/or as elements of the populated datastructure). A wide number of selection criteria can be utilized.

In one embodiment, a similarity index can be used as a selection criterion. Thus newly generated concatenated character strings must share a particular predefined similarity (e.g., greater than 10%, preferably greater than 20% or 30%, more preferably greater than 40% or 50% and most preferably greater than 60%, 70%, 80%, or even 90%) with each other and/or with the initial strings (or the encoded molecules) and/or with one or more "reference" strings.

Selection can also involve the use of algorithms that evaluate "relatedness" even when sequence identity is quite low. Such methods include "threading" algorithms and/or covariance measures.

Other selection criteria can require that the molecule(s) represented by the concatenated strings meet certain computationally predicted properties. Thus, for example selection criteria could require a minimum or maximum molecular weight, a certain minimum or maximum free energy in a particular buffer system, a minimum or maximum contact surface with a particular target molecule or surface, a particular net charge in a certain buffer system, a predicted PK, PI, binding avidity, particular secondary or tertiary forms, etc.

Still other selection criteria can require that the molecule(s) represented by the concatenated strings meet certain empirical physically assayed properties. Thus, for example, selection criteria could require that the molecule represented by the concatenated string have a certain temperature stability, level of enzymatic activity, produce a solution of a particular pH, have a particular temperature and/or pH optima, have a minimum or maximum solubility in a particular solvent system, bind a target molecule with a minimum or maximum affinity, and so forth. The physical determination of particular selection criteria typically requires that the molecule(s) represented by the concatenated string(s) be synthesized (e.g. chemically or by recombinant methods) or isolated.

The application of such selection criteria in physical systems is known to those of skill in the art (see, e.g., Stemmer et al., (1999) Tumor Targeting 4: 1–4; Ness et al. (1999) Nature Biotechnology 17: 893–896; Chang et al. (1999) Nature Biotechnology 17: 793–797; Minshull and Stemmer (1999) Current Opinion in Chemical Biology 3: 284–290; Christians et al. (1999) Nature Biotechnology 17: 259–264; Crameri et al. (1998) Nature 391: 288–291; Crameri et al. (1997) Nature Biotechnology 15: 436–438; Zhang et al. (1997) Proc. Natl. Acad. Sci., USA, 94: 4504–4509; Patten et al. (1997) Curr. Opin. Biotech. 8: 724–733; Crameri et al. (1996) Nature Med. 2:100–103; Crameri et al. (1996) Nature Biotechnology 14: 315–319; Gates et al. (1996) J. Mol. Biol. 255:373–386; Stemmer (1996) Crameri and Stemmer (1995) BioTechniques 18: 194–195; U.S. Pat. Nos. 5,605,793, 5,811,238 5,830,721, 5,834,252, 5,837,458, WO 95/22625, WO 97/0078, WO 97/35966, WO 99/41402; WO 99/41383, WO 99/41369, WO 9941368, EP 0934999; EP 0932670; WO 9923107; WO 9921979; WO 9831837; WO 9827230, and WO9813487).

VI. Introduction of Additional Variation.

In certain instances it is desired to introduce additional variation into the population. This is particularly desired where repeated iterations of an evolutionary algorithm using the initial population generated by the methods of this invention does not provide a solution to the modeled problem (e.g. no member meets a selection criterion).

Many methods can be used to introduce variation into the string population generated according to the methods of this invention. It is noted that variation can be introduced into the initial string(s) (input to the method) or into the concatenated string(s) (output). Preferably such variation will be introduced prior to a selection step, however in certain cases, variation may be introduced after selection (e.g. before a second iteration).

In one approach, a stochastic operator is introduced into the algorithm that randomly/haphazardly alters the one or more subunits comprising an encoded molecule. It is noted that variation can be introduced into the unencoded molecule (which is then re-encoded into a character string) and/or the variation can be introduced directly into the encoded character string. The stochastic operator typically invokes two selection processes. One selection process involves the determination of which subunit(s) to alter, while other selection process involves a selection/determination of what the subunit(s) are to be altered into. Both selection processes can be stochastic or alternatively on selection process or the other can be determinant. Thus, for example, the selection of the subunit(s) to "mutate" can be random/haphazard, but the mutation can always be into the same new/replacement subunit. Alternatively, the particular subunits that are to be mutated can be predetermined, but the selection of the mutated/resultant subunit can be random/haphazard. Still in another embodiment, both the selection of the subunit to mutate and the result of the mutation can be random/haphazard.

In preferred embodiments, the stochastic operator will also take as an input or parameter a "mutation frequency" that sets the average frequency of occurrence of a "mutation". Thus, for example, where the mutation frequency is set at 10%, the stochastic operator will only permit a mutation in one out of 10 subunits comprising in the initial strings. The mutation frequency can also be set as a range (e.g. 5%–10%, etc.).

The "stochastic operator" need not be applied to every initial string nor to every substring comprising an initial string. Thus, in certain embodiments, the action of the stochastic operator will be constrained to particular initial strings and/or to particular substrings (e.g. domains) of one or more initial strings.

Where both selection criteria of the stochastic operator are fixed, the operator is no longer stochastic, but rather introduces a "directed mutation". Such an operator may direct that every subunit "A" that the operator encounters is changed into a subunit "B". The directed mutation operator can still take a mutation frequency as a parameter/attribute/input. As described above, the mutation frequency will limit the number of "encountered" subunits that the operator actually transforms.

It will also be appreciated that the stochastic operator, as described above, can alter more than a single encoded subunit. In certain embodiments, the operator alters multiple encoded subunits or even entire substrings/domains.

Variation can also be introduced by the use of insertion or deletion operators. Insertion or deletion operators are essentially variants of "stochastic mutation" operators. Instead of transforming one or more subunits, a deletion operator removes one or more subunits, while an insertion operator inserts one or more subunits. Again deletion and insertion operators have two selection processes; One process that selects the site of the insertion or deletion and another process that selects the size of the deletion or the identity of the insertion. One or both selection processes can be stochastic. Where both selection processes are predetermined (non-stochastic) the insertion or deletion operators are directed insertion or directed deletion operators. As with the stochastic operator, the insertion or deletion operators can take a mutation frequency as a parameter/attribute/input.

In another embodiment, variation can be increased by adding one or more initial strings that are randomly or haphazardly generated and bear no necessary relationship to the initial strings derived from biological molecule(s). The variation-introducing initial string(s) can be produced as a strictly random or haphazard string or, in certain embodiments, the variation string(s) are produced according to certain predetermined criteria (e.g. frequency of occurrence of particular subunits, minimum and/or maximum degree of similarity with the encoded strings, etc.). The variation-introducing initial strings need not be full-length strings, but can also simply include one or more substrings. It will be noted that strings or substrings of this nature can be used to reduce variation as well. Thus, where a particular molecular domain is "favored" strings or substring(s) encoding this domain can be added to the population of initial strings.

VII. Populating a Data Structure.

In one embodiment, all the concatenated string(s) produced by the methods of this invention are used to populate a data structure and/or are used as initial strings in another iteration of the methods described herein. In other embodiments, selection criteria are imposed as described above, and only concatenated strings meeting the selection criteria are used as initial strings and/or are used to populate a data structure. The data structure can be populated with the concatenated representation of the encoded molecule(s) used in the above-described manipulations, or alternatively, the concatenated strings can be partially deconvolved to reproduce as simpler encoded or direct representation of the encoded biological molecules and these deconvolved strings can be used to populate the data structure.

In one embodiment, the data structure can be as simple as a piece of paper having the concatenated strings written out on it or a collection of cards each card listing one or more of the concatenated strings. In a preferred embodiment, the data structure is embodied in media (e.g. mechanical and/or fluid and/or optical and/or quantum and/or magnetic and/or electronic) that permit manipulation of the data structure by an appropriately designed computer. In particularly preferred embodiments, the data structure is formed in computer memory (e.g., dynamic, static, read-only, etc.) and/or in optical, magnetic, or magneto-optical storage media.

The data structure, even in a computer accessible form, can simply provide a list of the concatenated strings. Alternatively, the data structure can be structured to preserve relationships between the various "entries". At a simple level this can entail maintaining a simple identity and/or order of entries. More sophisticated data structures are also available and may provide ancillary structures for indexing and/or sorting and/or maintaining relationships between one or more entries in the data structure (e.g., concatenated strings). The data structure can additionally contain annotations regarding the entry (e.g. origin, type, physical properties, etc.), or links between an entry and an external data source. Preferred data structures include, but are not limited to lists, linked lists, tables, hash tables and other indexes, flat-file databases, relational databases, local or distributed computation systems. In particularly preferred embodiments, the data structure is a data file stored on conventional (e.g. magnetic and/or optical) media or read into a computer memory.

VIII. Embodiment in a Programmed Digital Apparatus

The invention may be embodied in a fixed media or transmissible program component containing logic instructions and/or data that when loaded into an appropriately configured computing device cause that device to populate a data structure (e.g. generate a pool/collection of concatenated strings) according to the methods of this invention.

Figure 4:
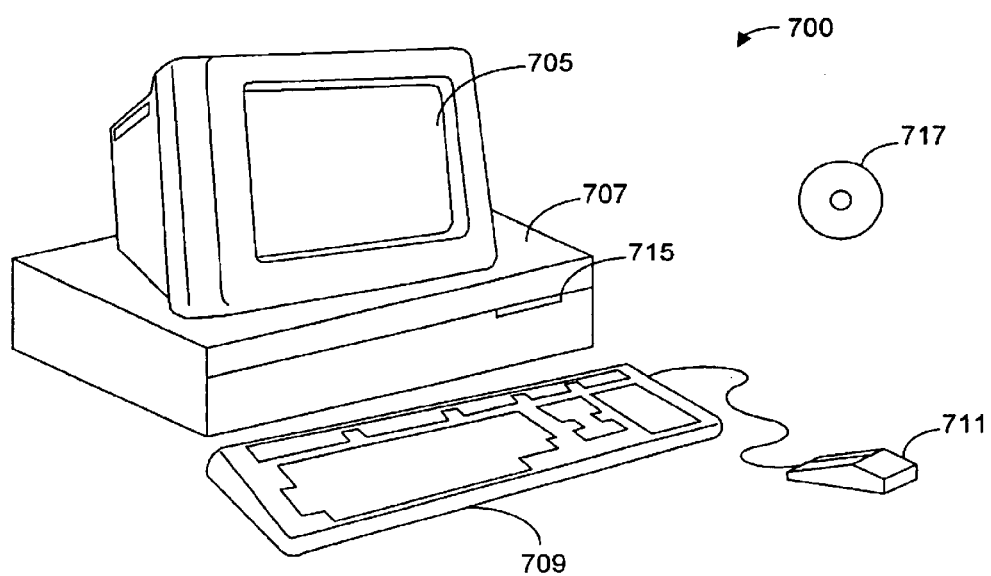
FIG. 4 illustrates a representational digital device 700 according to the present invention.

FIG. 4 shows digital device 700 that may be understood as a logical apparatus that can read instructions from media 717 and/or network port 719. Apparatus 700 can thereafter use those instructions to direct a encoding of biological molecules manipulation of the encoded representation(s) of the molecules and population of a data structure. One type of logical apparatus that may embody the invention is a computer system as illustrated in 700, containing CPU 707, optional input devices 709 and 711, disk drives 715 and optional monitor 705. Fixed media 717 may be used to program such a system and could represent a disk-type optical or magnetic media or a memory. Communication port 719 may also be used to program such a system and could represent any type of communication connection.

The invention also may be embodied within the circuitry of an application specific integrated circuit (ASIC) or a programmable logic device (PLD). In such a case, the invention may be embodied in a computer understandable descriptor language which may be used to create an ASIC or PLD that operates as herein described.

The invention also may be embodied within the circuitry or logic processes of other digital apparatus, such as cameras, displays, image editing equipment, etc.

IX. Embodiment in a Web Site.

The methods of this invention can be implemented in a localized or distributed computing environment. In a distributed environment, the methods may implemented on a single computer comprising multiple processors or on a multiplicity of computers. The computers can be linked, e.g. through a common bus, but more preferably the computer(s) are nodes on a network. The network can be a generalized or a dedicated local or wide-area network and, in certain preferred embodiments, the computers may be components of an intra-net or an internet.

In a preferred internet embodiment, a client system typically executes a Web browser and is coupled to a server computer executing a Web server. The Web browser is typically a program such as IBM's Web Explorer, or NetScape or Mosaic. The Web server is typically, but not necessarily, a program such as IBM's HTTP Daemon or other WWW daemon. The client computer is bi-directionally coupled with the server computer over a line or via a wireless system. In turn, the server computer is bi-directionally coupled with a website (server hosting the website) providing access to software implementing the methods of this invention.

A user of a client connected to the Intranet or Internet may cause the client to request resources that are part of the web site(s) hosting the application(s) providing an implementation of the methods of this invention. Server program(s) then process the request to return the specified resources (assuming they are currently available). A standard naming convention has been adopted, known as a Uniform Resource Locator ("URL"). This convention encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

The software implementing the method(s) of this invention can run locally on the server hosting the website in a true client-server architecture. Thus, the client computer posts requests to the host server which runs the requested process(es) locally and then downloads the results back to the client. Alternatively, the methods of this invention can be implemented in a "multi-tier" format wherein a component of the method(s) are performed locally by the client. This can be implemented by software downloaded from the server on request by the client (e.g. a Java application) or it can be implemented by software "permanently" installed on the client.

In one embodiment the application(s) implementing the methods of this invention are divided into frames. In this paradigm, it is helpful to view an application not so much as a collection of features or functionality but, instead, as a collection of discrete frames or views. A typical application, for instance, generally includes a set of menu items, each of with invokes a particular frame—that is, a form which manifest certain functionality of the application. With this perspective, an application is viewed not as a monolithic body of code but as a collection of applets, or bundles of functionality. In this manner from within a browser, a user would select a Web page link which would, in turn, invoke a particular frame of the application (i.e., subapplication). Thus, for example, one or more frames may provide functionality for inputing and/or encoding biological molecule(s) into one or more character strings, while another frame provides tools for generating and/or increasing diversity of the encoded character string(s).

In addition to expressing an application as a collection of frames, an application is also expressed as a location on the Intranet and/or Internet; a URL (Universal Resource Locator) address pointing the application. Each URL preferably includes two characteristics: content data for the URL (i.e., whatever data is stored on the server) together with a data type or MIME (Multipurpose Internet Mail Extension) type. The data type allows a Web browser to determine how it should interpret data received from a server (e.g., such as interpreting a .gif file as a bitmap image). In effect, this serves as a description of what to do with the data once it is received at the browser. If a stream of binary data is received as type HTML, the browser renders it as an HTML page. If instead it is received type bitmap, on the other hand, the browser renders it as a bitmap image, and so forth.

In Microsoft Windows, different techniques exist for allowing a host application to register an interest in a data object (i.e., data of a particular type). One technique is for the application to register with Windows an interest in a particular file extension for an (e.g., .doc—"Microsoft Word Document"); this is the most common technique employed by Window applications. Another approach, employed in Microsoft Object Linking and Embedded (OLE), is the use of a class Globally Unique Identifier or GUID—a 16-byte identifier for indicating a particular server application to invoke (for hosting the document having the GUID). The class ID is registered on a particular machine as being connected to a particular DLL (Dynamic Link Library) or application server.

In one embodiment of particular interest, a technique for associating a host application with a document is through a use of MIME types. MIME provides a standardized technique for packaging a document object. It includes a MIME header for indicating which application is appropriate for hosting the document, all contained in a format suitable for transmission across the Internet.

In one preferred embodiment, the methods of the present invention are implemented, in part, with the use of a MIME type specific to the use of the methods of this invention. The MIME type contains information necessary to create a document (e.g., Microsoft ActiveX Document) locally but, in addition, also includes information necessary to find and download the program code for rendering the view of the document, if necessary. If the program code is already present locally, it need only be downloaded for purpose of updating the local copy. This defines a new document type which includes information supporting downloadable program code for rendering a view of the document.

The MIME type may be associated with a file extension of APP. A file with the .APP extension is an OLE Document, implemented by an OLE DocObject. Because the .APP file is a file, it can be placed on a server and linked to using an HTML HREF. The .APP file preferably contains the following pieces of data: (1) the CLSID of an ActiveX object, which is an OLE Document Viewer implemented as one or more forms appropriate to the use of the methods of this invention; (2) the URL of the codebase where the object's code can be found, and (3) (optionally) a requested version number. Once the APP DocObject handler code is installed and registers the APP MIME type, it can be used to download an .APP file into the user's Web browser.

On the server side, since the APP file is really a file, the Web server simply receives the request and returns the file to the client. When the APP file is downloaded, the .APP DocObject handler asks the operating system to download the codebase for the object specified in the APP file. This system functionality is available in Windows through the CoGetClassObjectFromURL function. After the ActiveX object's codebase is downloaded, the .APP DocObject handler asks the browser to create a view on itself, for instance, by calling the ActivateMe method on the Explorer document site. The Internet Explorer then calls the DocObject back to instantiate a view, which it does by creating an instance of the ActiveX view object from the code that was downloaded. Once created, the ActiveX view object gets in-place activated in the Internet Explorer, which creates the appropriate form and all its child controls.

Once the form is created, it can establish connections back to any remote server objects it needs to perform its functions. At this point, the user can interact with the form, which will appear embedded in the Internet Explorer frame. When the user changes to a different page, the browser assumes responsibility for eventually closing and destroying the form (and relinquishing any outstanding connections to the remote servers).

In one preferred embodiment, from an end-user's desktop, the entry point to the system is the corporate home or the home page of another particular web-site. The page can, optionally, include, in a conventional manner, a number of links. In response to the user clicking on a particular link to an application page (e.g. a page providing the functionality of the methods of this invention), the web browser connects to the application page (file) residing on the server.

In one embodiment, where the user requests access to the methods of this invention, the user is directed to a particular page type, e.g., an application (appdoc) page for in-place execution of an application (implementing one or more elements of the methods of this invention) in the Web browser. Since each application page is located using an URL, other pages can have hyperlinks to it. Multiple application pages can be grouped together by making a catalog page that contains hyperlinks to the application pages. When the user selects a hyperlink that points to to an application page, the Web browser downloads the application code and executes the page inside the browser Upon the browser downloading the application page, the browser (based on the defined MIME type) invokes a local handler, a handler for documents of a type. ore particularly, the application page preferably includes a Globally Unique Identifier (GUID) and a codebase URL for identifying a remote (downloadable) application to invoke for hosting the document. Given the document object and the GUID which arrive with the application page, the local handler looks to the client machine to see if the hosting application already resides locally (e.g., by examining Windows 95/NT registry). At this point the local handler can choose to invoke a local copy (if any) or download the latest version of the host application.

Different models of downloading code are commonly available. When code is downloaded, a "code base" specification (file) is initially requested from the server. The code base itself can range from a simple DLL file to a Cabinet file (Microsoft cab file) containing multiple compressed files. Still further, an information (e.g., Microsoft .inf) file can be employed for instructing the client system how to install the downloaded application. These mechanisms afford great flexibility in choosing which component of an application gets downloaded and when.

For preferred embodiments, the machinery employed for actually downloading program code itself relies on standard Microsoft ActiveX API (Application Programming Interface)-calls. Although the ActiveX API does not provide native support for Web-delivered applications, its API can be invoked for locating the correct version of the program code, copying it to the local machine, verifying its integrity, and registering it with the clients operating system. Once the code has been downloaded, the handler can proceed to invoke the now-present application host for rendering the document object (in a manner similar to invoking the hosting application through the registry if it were already installed).

Now that the hosting application (OLE server) is loaded at the client, the client system can employ the OLE document view architecture to render the application correctly within the browser, including using conventional OLE methodology for adding the application's menu to that of the browser and for correctly re-sizing the application upon a re-size of the browser (as oppose to requiring the application to execute within a single Active X control rectangle—the limitation previously noted). Once the application is executing at the client, it can execute remote logic such as using RPC (Remote Procedure Call) methodology. In this manner logic which is preferably implemented as remote procedure(s) can still be used.

In particular preferred embodiments, the methods of this invention are implemented as one or more frames providing the following functionality. Function(s) to encode two or more a biological molecules into character strings to provide a collection of two or more different initial character strings wherein each of said biological molecules comprises at least about 10 subunits; functions to select at least two substrings from the character strings; functions to concatenate the substrings to form one or more product strings about the same length as one or more of the initial character strings; and functions to add (place) the product strings to a collection of strings.

The functions to encode two or more biological molecules preferably provide one or more windows wherein the user can insert representation(s) of biological molecules. In addition, the encoding function also, optionally, provides access to private and/or public databases accessible through a local network and/or the intranet whereby one or more sequences contained in the databases can be input into the methods of this invention. Thus, for example, in one embodiment, where the end user inputs a nucleic acid sequenced into the encoding function, the user can, optionally, have the ability to request a search of GenBank and input one or more of the sequences returned by such a search into the encoding and/or diversity generating function.

Methods of implementing Intranet and/or Intranet embodiments of computational and/or data access processes are well known to those of skill in the art and are documented in great detail (see e.g., Cluer et al. (1992) *A General Framework for the Optimization of Object-Oriented Queries, Proc SIGMOD International Conference on Management of Data, San Diego, Calif. Jun. 2–5, 1992, SIGMOD Record, vol. 21, Issue 2, June, 1992; Stonebraker, M., Editor ACM Press pp. 383–392; ISO-ANSI, Working Draft, "Information Technology-Database Language SQL", Jim Melton, Editor, International Organization for Standardization and American National Standards Institute, July 1992; Microsoft Corporation, "ODBC 2.0 Programmer's Reference and SDK Guide. The Microsoft Open Database Standard for Microsoft Widows.TM. and Windows NT.TM., Microsoft Open Database Connectivety.TM. Software Development Kit", 1992, 1993, 1994 Microsoft Press, pp. 3–30 and 41–56; ISO Working Draft, "Database Language SQL-Part 2: Foundation (SQL/Foundation)", CD9075-2:199.chi.SQL, Sep. 11, 1997, and the like).

Those skilled in the art will recognize many modifications may be made to this configuration without departing from the scope of the present invention. For example, in a two-tier configuration, the server system executing the functions of the WWW gateway may also execute the functions of the Web server. For example, any one of the above described embodiments could be modified to accept requests from users/user terminals that are in a format other than a URL. Yet another modification would involve the adaptation to a multi-manager environment.

X. Incorporating a Physical Evaluation and Feedback Loop.

As indicated above, in certain preferred embodiments, the selection criteria can require that the molecule(s) represented by the concatenated strings meet certain empirical physically assayed properties. To assay these properties it is necessary to obtain the encoded molecules. To accomplish this, the molecule(s) represented by the concatenated string(s) are physically synthesized (e.g. chemically or by recombinant methods) or isolated.

Physical synthesis of genes, proteins, polysaccharides encoded by the collection(s) of character strings produced according to the present invention is the primary means to create a physical representation of matter that is amenable to a physical assay for one or more desired properties.

In a preferred embodiment, gene synthesis technology is used, typically, to construct libraries in a consistent manner and in close adherence to the sequence representations provided in the collection of concatenated strings produced by the methods of this invention.

Preferred gene synthesis methods allow fast construction of libraries of $10^4$–$10^9$ "gene/protein" variation. This is typically adequate for screening/selection protocols as larger libraries are more difficult to make and maintain and sometimes cannot be as completely sampled by a physical assay or selection methods. For example, existing physical assay methods in the art (including, e.g., "life-and-death" selection methods) generally allow sampling of about $10^9$ variations or less by a particular screen of a particular library, and many assay are limited to sampling about $10^4$–$10^5$ members. Thus, building several smaller libraries is a preferred method as large libraries cannot easily be completely sampled. Larger libraries, however, can also be made and sampled, e.g., using high-throughput methods.

There are many methods which can be used to synthesize genes, polysaccharides, proteins, etc. with well-defined sequences and the area is quickly developing. Solely, for the purpose of clarity of illustration, this discussion will focus on one of the many possible and available types of known methods for the production of biological molecules.

Current art in the polynucleotide synthesis is best represented by well-known and mature phosphoramidite chemistry which allows one of skill to effectively prepare oligonucleotides. It is possible, but somewhat impractical to use this chemistry for routine synthesis of oligonucleotides significantly longer than 100 bp and the synthetic yield decreases and the degree of purification required increases. Oligonucleotides of a "typical" 40–80 bp size can be obtained routinely and directly with very high purity.

It is noted that oligonucleotides and even complete synthetic (double stranded or single stranded) genes can be ordered from any of a number of commercial sources such as The Midland Certified Reagent Company (3112-A West Cuthbert Avenue, Midland, Tex. 79701). The Great American Gene Company (1130 D Street, Suite #8, Ramona, Calif. 92065), ExpressGen, Inc. (CTP Research Center, 2201 West Campbell Park Drive, Chicago Ill. 60612-3501), Operon Technologies Inc. 1000 atlantic Ave. Alameda, Calif., and many others. Similarly, peptides can be custom ordered from any of a variety of sources such as PeptidoGenic Research and Development Company. HTI Bio-products, Inc., BMA Biomedicals, Ltd. (U.K., Bio-Synthesis, Inc.), and many others.

A relevant demonstration of total gene synthesis from small fragments which is readily amendable to optimization, parallelism, and high throughput is set forth by Dillon and Rosen (1990) *Biotechniques,* 9(3): 298–300. A simple and rapid PCR-based assembly process of a gene from a set of partially overlapping single-strand oligonucleotides without the use of ligase is described. Several groups have also described successful application of variations of the same PCR-based gene assembly approach to the synthesis of various genes of increasing size, thus demonstrating the methods general applicability and combinatorial nature for synthesis of libraries of mutated genes (for useful references see also, Sandhu et al (1992) *Biotechniques,* 12(1): 15–16, Prodomou and Pearl (1992) *Protein Engin.,* 5(8): 827–829, Chen et al. (1994) *JACS,* 1194(11): 8799–8800, Hayashi et al. (1994) *Biotechniques,* 17: 310–314, and others).

More recently Stemmer et al. (1995) *Gene* 1645: 49–53, provided evidence that PCR-based assembly methods are useful to build larger genes of up to at least 2.7 kb from dozens or even hundreds of synthetic 40 bp oligonucleotides. These authors also demonstrated that, from the four steps comprising the known PCR-based gene synthesis protocol (oligonucleotide synthesis, gene assembly, gene amplification, and typically, cloning) the gene amplification step can be omitted if a "circular" assembly PCR is used.

Once prepared, the gene(s) can be inserted into vectors and the vectors used to transfect host cells and express the encoded protein(s) according to routine methods well known to those of skill in the art. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* Vol. 152 Academic Press, Inc., San Diego, Calif. (Berger); Sambrook et al. (1989) *Molecular Cloning_A Laboratory Manual* (*2nd ed.*) Vol. 1–3, Cold Spring Harbor Laboratory, Cold Spring Harbor Press, NY; and *Current Protocols in Molecular Biology,* F. M. Ausubel et al., eds., Current Protocols, a joint venture between Greene Publishing Associates, Inc. and John Wiley & Sons, Inc., (1994 Supplement). Product information from manufacturers of biological reagents and experimental equipment also provide information useful in known biological methods. Such manufacturers include the SIGMA chemical company (Saint Louis, Mo.), R&D systems (Minneapolis, Minn.), Pharrnacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica Biochemika Analytika (Fluka Chemie AG, Buchs, Switzerland), Invitrogen, San Diego, Calif., and Applied Biosystems (Foster City, Calif.), as well as many other commercial sources known to one of skill.

The physical molecules, once expressed can be screened for one or more properties and it can be determined whether or not they meet the selection criteria. The character strings encoding molecules meeting the physical selection criteria are then selected as described above. Numerous assays for physical properties (e.g. binding specificity and/or avidity, enzymatic activity, molecular weight, charge, thermal stability, temperature optima, pH optima, etc.) are well known to those of skill in the art.

In certain embodiments, the physical molecules can be subject to one or more "shuffling" procedures and optionally screened for particular physical properties, to generate new molecules which can then be encoded and processed according to the methods described above.

A variety of "shuffling methods" are known, including those taught by the inventors and their coworkers, e.g. Stemmer, et al. (1994) *Nature* 370: 389–391, Stemmer (1994) *Proc. Natl. Acad. Sci., USA,* 91: 10747–10751, Stemmer, U.S. Pat. No. 5,603,793, Stemmer et al. U.S. Pat. No. 5,830,721, Stemmer et al U.S. Pat. No. 5,811,238, Minshull et al. U.S. Pat. No. 5,837,458, Crameri et al. (1996) *Nature Med.,* 2(1): 100–103, PCT Publications WO 95/22625, WO 97/20078, WO 96/33207, WO 97/33957, WO 98/27230, WO 97/35966, WO 98/31837, WO 98/13487, WO 98/13485 and WO 98/42832. In addition, several copending applications describe important DNA shuffling methodologies (see, e.g., copending U.S. Ser. No. 09/116,188, filed Jul. 15, 1998, U.S. Ser. No. 60/102,362, and Selifonov and Stemmer Methods for making character strings, polynucleotides & polypeptides having desired characteristics filed Feb. 5, 1999, U.S. Ser. No. 60/118,854).

In addition, the methods described above can also be practiced in a parallel mode where each of the individual library members, including a plurality of the genes, proteins, polysaccharides, etc. for subsequent physical screening are synthesized in spatially segregated vessels or arrays of vessels, or in a poolwise manner where all, or part, of the desired plurality of molecules are synthesized in a single vessel. Many other synthetic approaches are known and specific advantages of one versus another may readily be determined by one skilled in the art.

The processes discussed herein are amenable to production using high-throughput systems. High throughput (e.g. robotic) systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configuarable systems provide high throughput and rapid start up as well as a high degree of flexibility and customization. The manufacturers of such systems provide detailed protocols the various high throughput. Thus, for example, Zymark Corp. provides technical bulletins describing the use of high throughput systems for cloning expression and screening of chemically or recombinantly produced products.

XI. Uses of the Generated String Population(s).

A) Use in Genetic/Evolutionary Algorithms.

In one embodiment the methods of this invention provide a population of character strings. Particularly preferred character strings represent encoded biological molecules and typically the encoded molecules bear some relationship to each other reflecting a level of biological organization. Consequently, the character strings produced by the methods of this invention do not reflect a random or haphazard selection from a uniform sequence space, but rather capture degrees of relatedness (or variation) reflective of that particular level of organization (e.g. gene, gene family, individual, subpopulation, etc.) found in the natural world. The collections of character strings (e.g. populated data structure) produced by the methods of this invention thus provide a useful starting point for various evolutionary models and are convenient for use in evolutionary algorithms (evolutionary computing).

When used in such models, the populations (collections of character strings) produced by the methods of this invention provide far more information than evolutionary algorithms run on arbitrary populations.

For example, where an evolutionary algorithm utilizes as a starting point, a population comprising a set of random or arbitrary members, the dynamics of the simulation reflect progression from the arbitrary starting point to a particular solution (e.g. distribution of properties in the resulting population(s)). Since the starting point is arbitrary and essentially unrelated to a population produced by a natural process, these dynamics afford no information regarding the dynamics of natural processes/populations.

In contrast, the collections of character strings produced by the methods of this invention contain far more information than the randomly produced starting points used in conventional evolutionary algorithms. First, each member of population contains considerable information regarding molecular structure. Thus, one member is distinguished from another member not simply as "self/not-self" (i.e., al allelic representation), but rather members are distinguished by degrees of relatedness/similarity. Members of the populations produced by the methods of this invention will reflect varying degrees of covariation.

In addition, because the populations produced by the methods of this invention reflect a fine structure characteristic of the level of biological organization encoded into the initial strings, the initial dynamics of a simulation run using these starting sets reflects the dynamics of "real world" populations and affords considerable insight into evolutionary processes.

In addition, because specific molecules are represented by members generated using the methods of this invention, evolutionary algorithms run using these data structures provides real information regarding molecular evolution and/or the design of new and useful molecular entities.

B) Use in Index Generation.

In another embodiment, the data structures generated by the methods of this invention can be used as tags (indices) for indexing essentially any kind of information. In this approach, information of greater similarity is tagged using members of the data structure (character strings) having greater similarity, while information of lower similarity is tagged with members of the data structure having lower similarity. In preferred embodiments, the similarity of the character strings used to tag two different pieces of data reflects (is proportional to) the similarity of tagged information.

When a search is performed, an initial hit is identified using traditional search techniques. Then, when closely related information is desired, the data structure can be searched for similar members using any of the well known similarity algorithms described above. These similarity algorithms are designed to provide a thorough, rapid, and efficient search of an enormous data space. When members (indices) of desired similarity are identified, they will point to the tagged data thereby providing the end user with related information.

C) Use as Reference Objects in Database Searches.

In a related application, the data structures produced by the methods of this invention, or the members of such data structures (i.e., the character strings) can be used as reference objects in database searches. For example, initial known information (e.g. molecular structure, or index strings from a knowledge database as described above) is encoded and modified according to the methods described herein. This produces a new data structure that captures related, but non-obvious variants of the initial encoded information.

The resulting information (e.g., members of the data structure) can be deconvolved to identify actual or theoretical molecule(s) and this can be used to search typical databases for the same or related molecules. Where the encoded information is from a database index, the member of the data structure can be used to probe the original or new database to identify relevant/related information.

D) Identification of Structural Motifs Conferring Specific Molecular Properties.

It is often of interest to identify regions of a molecule (e.g. a protein) that may be responsible for specific properties, e.g. to facilitate functional manipulation. This is traditionally done using structural information, usually obtained by x-ray crystallography.

The sequences of naturally occurring enzymes that catalyze similar or even identical reactions can vary widely; sequences may be only 50% identical or less, while a family of such enzymes may catalyze one identical reaction, other properties of these enzymes may differ significantly. These include physical properties such as stability to temperature and organic solvents, pH optima, solubility, ability to retain activity when immobilized, ease of expression in different host systems. They also include catalytic properties including activity ($K_{cat}$ and $K_m$), the range of substrates accepted, and even of chemistries performed. THE methods described here can also be applied to non-catalytic proteins (e.g. ligands such as cytokines) and even nucleic acid sequences (such as promoters that may be inducible by a number of different ligands), wherever multiple functional dimensions are encoded by a family of "homologous" sequences.

Because of the divergence between enzymes with similar catalytic functions, it is not usually possible to correlate specific properties with individual amino acids at certain positions. There are just too many amino acid differences. However, libraries of variants can be prepared from family of homologous natural sequences by encoding members of the family into initial strings according to the methods of this invention, then selecting and concatenating substrings to populate a data structure with encoded variants.

The encoded or deconvolved variants can be tested in silico for desired properties and/or the encoded variants can be deconvolved, and the corresponding molecule physically synthesized as described above. The synthesized molecule can then be screened for one or more desired properties.

If members of the data structure are tested under a specific set of conditions for a particular property, the optimal combinations of sequences from the data structure (or the initial string collection) for those conditions can be determined. If the assay conditions are altered in only one parameter, different individuals from the library (data structure) will be identified as the best performers. Because the screening conditions are very similar, most amino acids will probably be conserved between the two sets of best performers (the best performers in the initial string collection (set 1) and the best performers in the populated data structure (set 2)). Comparisons of the sequences of the best enzymes under the two different conditions will therefore identify the sequence differences responsible for the differences in performance.

Principle component analysis (e.g. using Partek type software) is one of many multi-variate tools useful for such an analysis.

E) Use in Generating Music.

In still another embodiment, the methods of this invention can be used to generate music. Using any of a number of well known programs, biological molecules (e.g. DNA, proteins, etc.) can be encoded into musical notes. This can involve mapping a particular subunit onto a particular note. The timing and/or timbre of the notes is determined by the motif and/or secondary structure in which the subunit occurs.

Thus for example, the program SS-midi has been used to encode various nucleic acid and amino acid sequences into music. In one approach (DNA calypso, purines were played 3/2 the speed of pyrimidines, the bases C, T, G, A were mapped to the notes C, F, G, A and the first strand was played with jazz organ, while the complementary strand with bass. In other approaches note duration can be longer when the note/subunit is found in a helix then when it is found in a β-sheet. Other variants are, of course, possible.

In the methods of this invention, the biological molecules are encoded into strings, the substrings selected and concatenated and the data structure populated as described above. The populated data structure is then used as input to a program (e.g., SS-midi) that maps the new sequences encoded in the data structure into music. The data structure can be iteratively repopulated as described above thereby generating variants of the musical phrases thus produced.

F) Use in Driving Synthetic Machinery

As indicated above, the data structures produced by the methods of this invention can be used to drive devices for the chemical synthesis of the encoded molecules (e.g. polypeptides, nucleic acids, polysaccharides, etc.). Using only a few initial sequences ("seed members") the methods of this invention provide literally tens, hundreds, thousands, tens of thousands, hundreds of thousands, or even millions of different encoded molecules. When the resulting data structure, or members thereof, is used to drive a chemical (or recombinant) synthesis a "combinatorial" library of the desired molecules of virtually any size can be prepared. Such "combinatorial" libraries are widely desired to provide systems for screening for therapeutics, industrial process molecules, particular enzymes, etc.

EXAMPLES

The following examples are offered to illustrate, but not to limit the claimed invention.

Example 1

Subtilisin Family Model

Figure 5:
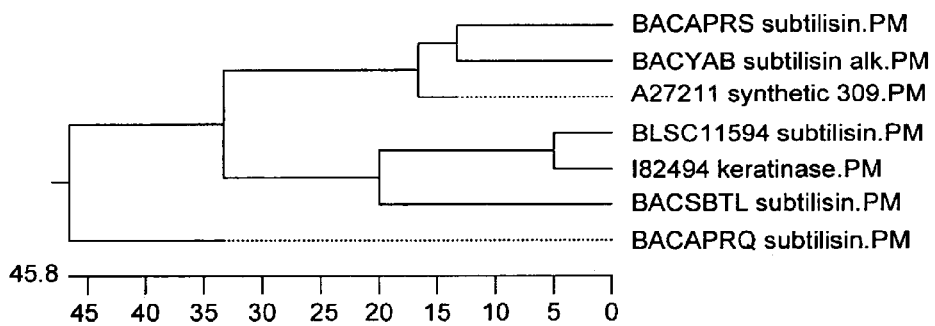
FIG. 5 is a chart and relational tree showing percent similarity for different subtilisins (an exemplar set of initial character strings).
Figure 6:
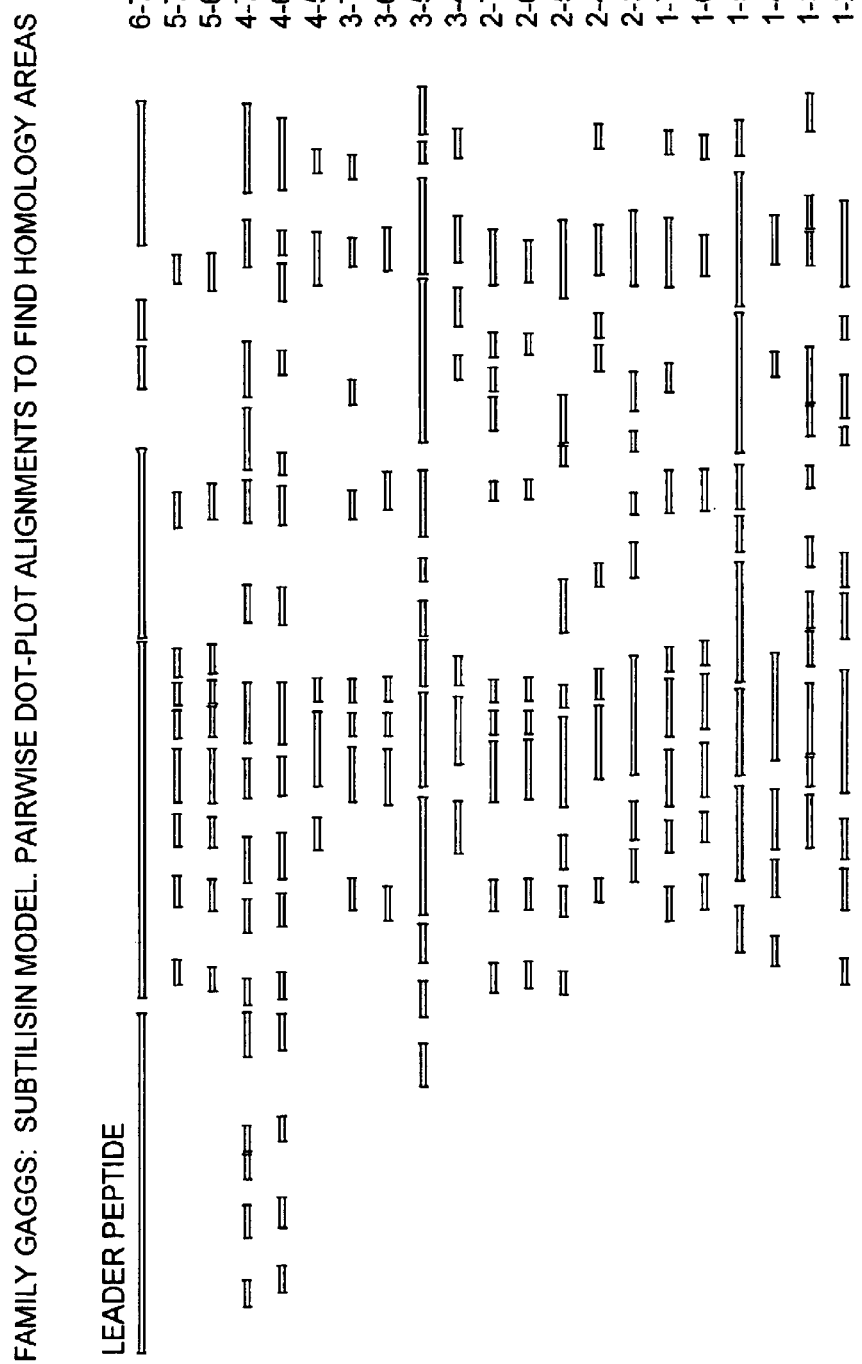
FIG. 6 is a pairwise dot-plot alignment showing homology areas for different subtilisins.
Figure 7:
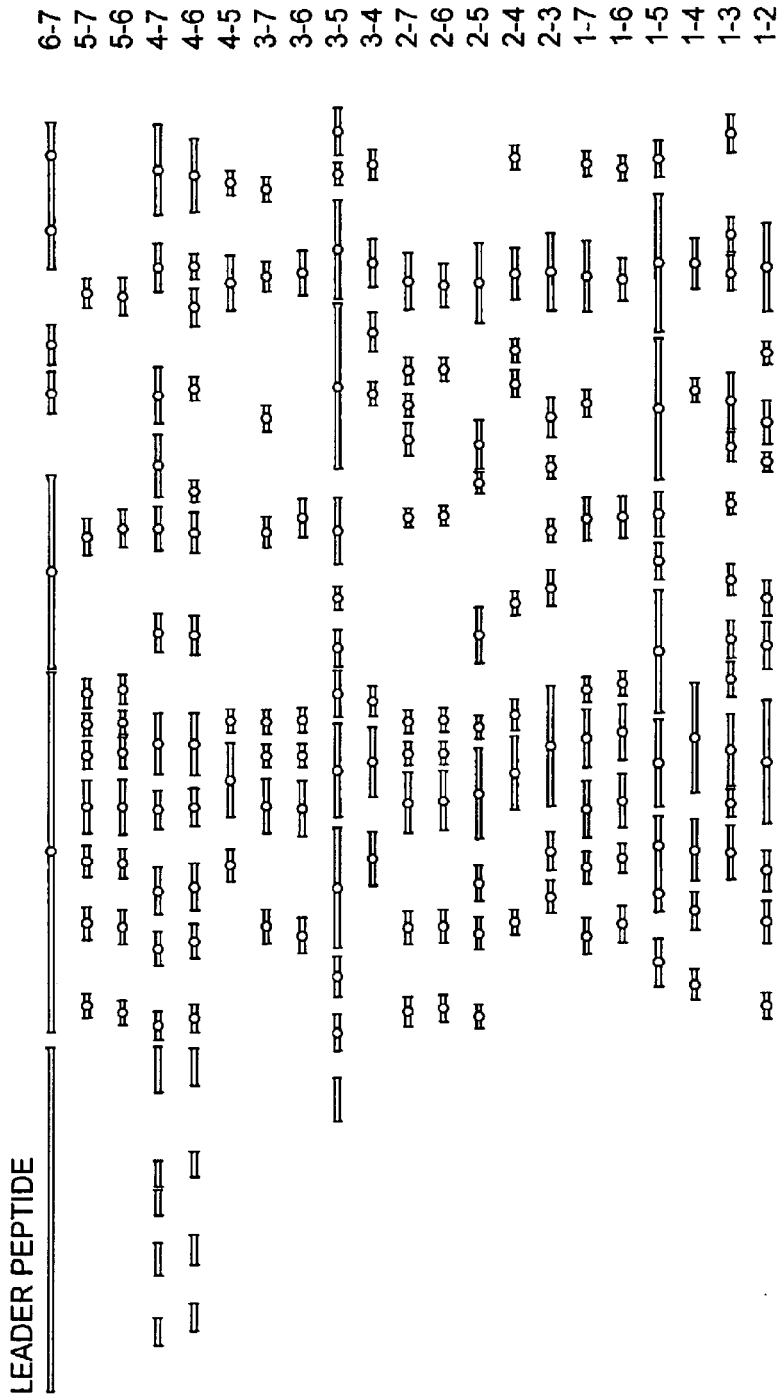
FIG. 7 is a pairwise dot-plot alignment showing homology areas for seven different parental subtilisins.

Amino acid sequences were aligned. (Codon usage can be optimized on retrotranslation for a preferred expression system, and number of oligonucleotides for synthesis can be minimized). A Dot plot pairwise alignment of all possible pairs of 7 parents was made (FIG. 5, 6, 7). Pair 6 and 7 showed 95% percent identity per each window of ≧7aa, while all other pairs showed 80% percent identity per each window of ≧7aa. Note that stringency of alignment (and subsequent representation of crossover between parents) can be manipulated individually for each pair, so that low homology crossover can be represented at the expense of highly homologous parents. No structural biases or active site biases were incorporated in this model.

Example 2

A Process for Design of Crossover Oligonucleotides for Synthesis of Chimerical Polynucleotides First, substrings are identified and selected in parental (initial) strings for applying a crossover operator to from chimeric junctions. This is performed by: a) identifying all or part of the pairwise homology regions between all parental character strings, b) selecting all or part of the identified pairwise homology regions for indexing at least one crossover point within each of the selected pairwise homology regions, c) selecting one or more of the pairwise nonhomology regions for indexing at least one crossover point within each of the selected pairwise nonhomology regions ("c" is an optional step which can be omitted, and is also a step where structure-activity based elitism can be applied), thereby providing a description of a set of positionally and parent-indexed regions/areas (substrings) of parental character strings suitable for further selection of crossover points.

Secondly, further selection of crossover points within each of the substrings of the set of the substrings selected in Part 1 is performed. The steps include: a) randomly selecting at least one of the crossover points in each of the selected substrings, and/or b) selecting at least one of the crossover points in each of the selected substrings, using one or more of annealing simulation-based models for determining probability of the crossover point selection within each of the selected substrings and/or c) selecting one crossover point approximately in the middle of each of the selected substrings, thereby creating a set of pairwise crossover points, where each point is indexed to corresponding character positions in each of the parental strings desired to from a chimeric junction at that point.

Thirdly, optional codon usage adjustments are performed. Depending on methods used to determine homology (strings encoding DNA or AA), the process can be varied. For example, if a DNA sequence was used: a) adjustment of codons for the selected expression system is performed for every parental string, and b) adjustment of codons among parents can be performed to standardize codon usage for every given amino acid at every corresponding position. This process can significantly decrease total number of distinct oligonucleotides for gene library synthesis, and may be particularly beneficial for cases where AA homology is higher than DNA homology, or with families of highly homologous genes (e.g. 80%+identical).

This option has to be exercised with caution, as it is in essence an expression of an elitism mutation operator. Thus, one considers the benefits of cutting the costs of oligonucleotides versus introduction of this bias, which can have undesirable consequences. Most typically, one uses codons which encode AA at a given position in a majority of parents.

If AA sequences are used: a) retrotranslate sequence to degenerate DNA; b) define degenerate nucleotides using position-by-position referencing to codon usage in original DNA (of majority of parents or of corresponding parent), and/or—exercise codon adjustments suitable for the selected expression system where a physical assay will be performed.

This step can also be used to introduce any restriction sites within coding parts of the genes, if any, for subsequent identification/QA/deconvolution/manipulations of library entries. All crossover points identified in Part 2 (indexed to pairs of parents) are correspondingly indexed to the adjusted DNA sequences.

Fourth, oligonucleotide arrangements are selected for a gene assembly scheme. This step includes several decision steps:

Uniform 40–60 mer oligonucleotides are typically used (using longer oligonucleotides will result in decrease of the number of oligonucleotides to build parents, but uses additional dedicated oligonucleotides for providing representation of closely positioned crossovers/mutations.

Select whether shorter or longer oligonucleotides are allowed (i.e., a Yes/No? decision). A "Yes" decision cuts the total number of oligonucleotides for high homology genes of different lengths with gaps (deletion/insertion), especially for 1–2aa).

Select the overlap length (typically 15–20 bases, which can be symmetrical or asymmetrical.) Select whether degenerate oligonucleotides are allowed (Yes/No?). Another potent cost cutting feature and also a powerful means to obtain additional sequence diversity. Partial degeneracy schemes and minimized degeneracy schemes are especially beneficial in building, mutagenic libraries.

If software tools are used for these operations, several variations of the parameters are run to select maximum library complexity and minimal cost. Exercising complex assembly schemes using oligonucleotides of various length significantly complicates indexing processes and, subsequently, assembly of the library in positionally encoded parallel or partial pooling formats. If this is done without sophisticated software, a simple and uniform scheme (e.g. all oligonucleotides 40 bases long with 20 bases overlap) can be used.

Fifth, "convenience sequences" are designed in front and in the back of the parent strings. Ideally, it is the same set which will be built in every library entry at the end. These include any restriction sites, primer sequences for assembled product identifications, RBS, leader peptides and other special or desirable features. In principle, the convenience sequences can be defined at a later stage, and at this stage, a "dummy" set of appropriate length can be used, e.g. a substring from an easily recognizable forbidden letters.

In Part 6 an indexed matrix of oligonucleotide strings for building every parent is created, according to the selected scheme. An index of every oligonucleotide includes: a parent identifier (parentID), indication of coding or complementary chain, and position numbers. Crossover points are determined for indexed coding string of every parent with head and tail convenience substrings. A complementary chain of every string is generated. Every coding string is selected according to the selected assembly PCR scheme in part 4 (e.g. in increments of 40 bp). Every complement string is split according to the same scheme (e.g. 40 bp with 20 bp shift).

In part 7, an indexed matrix of oligonucleotides is created for every pairwise crossover operation. First, all oligonucleotides which have pairwise crossover markers are determined. Second, all sets of all oligonucleotides which have the same position and same pair of parents crossover markers (4 per crossover point) are determined. Third, every set of 4 oligonucleotide strings are taken which have been labeled with the same crossover marker, and another derivative set of 4 chimeric oligonucleotide strings comprising of characters encoding 2 coding and 2 complement chains (e.g. with 20 bp shift in 40=20+20 scheme) are made. 2 Coding strings are possible, having a forward end sequence substring of one parent followed by the backward end of the second parent after crossover point. Complement strings are also designed in the same fashion, thereby obtaining an indexed complete inventory of strings encoding oligonucleotides suitable for gene library assembly by PCR.

This inventory can further be optionally refined by detecting all redundant oligonucleotides, counting them and deleting from inventory, accompanied by the introduction of the count value to the "abundance=amount" field in the index of each oligonucleotide string. This may be a very beneficial step for reducing total number of oligonucleotides for library synthesis, particularly in the cases if parental sequences are highly homologous.

Modifications can be made to the methods and materials as hereinbefore described without departing from the spirit or scope of the invention as claimed, and the invention can be put to a number of different uses, including:

The use of an integrated system to generate shuffled nucleic, acids and/or to test shuffled nucleic acids, included in an iterative process.

An assay, kit or system utilizing a use of any one of the selection strategies, materials, components, methods or substrates hereinbefore described. Kits will optionally additionally comprise instructions for performing methods or assays, packaging materials, one or more containers which contain assay, device or system components, or the like.

In an additional aspect, the present invention provides kits embodying the methods and apparatus herein. Kits of the invention optionally comprise one or more of the following: (1) a shuffled component as described herein; (2) instructions for practicing the methods described herein, and/or for operating the selection procedure herein; (3) one or more assay component; (4) a container for holding nucleic acids or enzymes, other nucleic acids, transgenic plants, animals, cells, or the like, (5) packaging materials, and (6) software for performing any of the process and/or decision steps noted herein.

In a further aspect, the present invention provides for the use of any component or kit herein, for the practice of any method or assay herein, and/or for the use of any apparatus or kit to practice any assay or method herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying molecules for production, wherein the molecules are represented by concatenated strings, said method comprising:

i) encoding two or more biological molecules into a data structure of initial character strings to provide a collection of two or more different initial character strings wherein each of said biological molecules comprises at least about 10 subunits;
 ii) selecting at least two substrings from said initial character strings;
 iii) concatenating said substrings to form one or more product strings about the same length as one or more of the initial character strings;
 iv) adding the product strings to a data structure to populate a data structure of product strings;
 v) determining sequence identities of at least one of the product strings relative to at least one initial character string; and
 vi) selecting one or more product biological molecules for production, wherein the one or more product biological molecules correspond to one or more of the product strings having greater than 30% sequence identity with the at least one initial character string.

2. The method of claim 1, wherein said encoding comprises encoding two or more nucleic acid sequences into said character strings.

3. The method of claim 2, wherein said two or more nucleic acid sequences comprise a nucleic acid sequence encoding a naturally occurring protein.

4. The method of claim 1, wherein said encoding comprises encoding two or more amino acid sequences into said character strings.

5. The method of claim 4, wherein said two or more amino acid sequences comprise an amino acid sequence encoding a naturally occurring protein.

6. The method of claim 1, wherein said initial character strings have at least 30% sequence identity with each other.

7. The method of claim 1, wherein said selecting in (ii) comprises selecting at least one substring from an initial character string such that the ends of said substring occur in string regions of about 3 to about 20 characters in the initial character string that have higher sequence identity with the corresponding region of another of said initial character strings than the overall sequence identity between the two initial character strings.

8. The method of claim 1, wherein said selecting in (ii) comprises selecting substrings such that the ends of said substrings occur in predefined motifs of about 4 to about 8 characters.

9. The method of claim 1, wherein said selecting in (ii) comprises aligning two or more of said initial character strings to maximize pairwise identity between two or more substrings of the initial character strings, and selecting a character that is a member of an aligned pair for the end of one of the two or more substrings.

10. The method of claim 1, wherein said method further comprises randomly altering one or more characters of said initial or product character strings.

11. The method of claim 10, wherein said method further comprises randomly selecting and altering one or more occurrences of a particular preselected character in said initial or product character strings.

12. The method of claim 1, wherein said encoding, selecting, or concatenating is performed on an internet site.

13. The method of claim 1, wherein said encoding, selecting, or concatenating is performed on a server.

14. The method of claim 1, wherein said encoding, selecting, or concatenating is performed on a client linked to a network.

15. The method of claim 1, wherein the initial character strings of (i) are related in that they encode the same gene or protein family but differ in sequence.

16. The method of claim 1, further comprising determining a computationally predicted property for molecules represented by the product strings.

17. The method of claim 1, wherein the molecules represented by the product strings are made in parallel in an array of vessels.

18. The method of claim 1, wherein the molecules represented by the product strings are made by assembly of oligonucleotides.

19. The method of claim 1, wherein the one or more product strings of (vi) have greater than 50% sequence identity with the at least one initial character string.

20. The method of claim 1, wherein the one or more product strings of (vi) have greater than 75% sequence identity with the at least one initial character string.

21. The method of claim 1, wherein the one or more product strings of (vi) have greater than 85% sequence identity with the at least one initial character string.

22. The method of claim 1, wherein the one or more product strings of (vi) have greater than 90% sequence identity with the at least one initial character string.

23. The method of claim 1, wherein the one or more product strings of (vi) have greater than 95% sequence identity with the at least one initial character string.

24. The method of claim 1, wherein adding the product strings to a data structure comprises adding more than one product string to the data structure.

25. The method of claim 1, wherein selecting at least two substrings from said initial character strings comprises random substring selection.

26. The method of claim 1, wherein selecting at least two substrings from said initial character strings comprises uniform substring selection.

27. The method of claim 1, wherein selecting at least two substrings from said initial character strings comprises motif-based selection.

28. The method of claim 1, wherein selecting at least two substrings from said initial character strings comprises alignment-based selection.

29. The method of claim 1, wherein selecting at least two substrings from said initial character strings comprises frequency-biased selection.

30. A computer program product on a computer readable media comprising computer code that:
   i) encodes two or more biological molecules into initial character strings to provide a collection of two or more different initial character strings wherein each of said biological molecules comprises at least about ten subunits;
   ii) selects at least two substrings from said initial character strings;
   iii) concatenates said substrings to form one or more product strings about the same length as one or more of the initial character strings;
   iv) adds the product strings to a data structure to populate a data structure of product strings;
   v) determines sequence identities of at least one of the product strings relative to at least one initial character string; and
   vi) selects one or more product biological molecules for production, wherein the one or more product biological molecules correspond to one or more of the product strings having greater than 30% sequence identity with the at least one initial character string.

31. The computer program product of claim 30, wherein said two or more biological molecules are nucleic acid sequences.

32. The computer program product of claim 30, wherein said two or more biological molecules are nucleic acid sequences encoding naturally occurring proteins.

33. The computer program product of claim 30, wherein said two or more biological molecules are amino acid sequences.

34. The computer program product of claim 30, wherein said initial character strings have at least 30% sequence identity with each other.

35. The computer program product of claim 30, wherein said computer code selects in (ii) at least one substring from an initial character string such that the ends of said substring occur in string regions of about three to about twenty characters in the initial character string that have higher sequence identity with a corresponding region of another of said initial character strings than the overall sequence identity between the two initial character substrings.

36. The computer program product of claim 30, wherein said computer code selects substrings such that the ends of said substrings occur in predefined motifs of about 4 to about 8 characters.

37. The computer program product of claim 30, wherein the computer code selects substrings by aligning two or more of said initial character strings to maximize pairwise identity between two or more substrings of the character strings, and selecting a character that is a member of an aligned pair for the end of one substring.

38. The computer program product of claim 30, wherein said computer code additionally randomly alters one or more characters of said initial or product character strings.

39. The computer program product of claim 38, wherein said computer code additionally randomly selects and alters one or more occurrences of a particular preselected character in said initial or product character strings.

40. The computer program product of claim 30, wherein said computer code is stored on media selected from the group consisting of magnetic media, optical media, and optomagnetic media.

41. The computer program product of claim 30, wherein said computer code is in dynamic or static memory of a computer.

42. The computer program product of claim 30, wherein the initial character strings of (i) are related in that they encode the same gene or protein family but differ in sequence.

43. The computer program product of claim 30, wherein the code instructs physical screening of the molecule(s) represented by the product strings for one or more desired properties.

44. The computer program product of claim 30, wherein the code instructs determination of a computationally predicted property for molecules represented by the product strings.

45. The computer program product of claim 30, wherein the code tests members of the data structure of product strings for a particular property and determines sequence differences responsible for differences in the particular property using multi-variate analysis.

46. The computer program product of claim 30, wherein the one or more product strings of (vi) having greater than 50% sequence identity with the at least one initial character string.

47. The computer program product of claim 30, wherein the one or more product strings of (vi) having greater than 75% sequence identity with the at least one initial character string.

48. The computer program product of claim 30, wherein the one or more product strings of(vi) having greater than 95% sequence identity with the at least one initial character string.

49. The computer program product of claim 30, wherein the computer code adds the product strings to a data structure by adding more than one product string to the data structure.

50. The computer program product of claim 30, wherein the computer code selects at least two substrings from said initial character strings by a random substring selection.

51. The computer program product of claim 30, wherein the computer code selects at least two substrings from said initial character strings by a uniform substring selection.

52. The computer program product of claim 30, wherein the computer code selects at least two substrings from said initial character strings by a motif-based selection.

53. The computer program product of claim 30, wherein the computer code selects at least two substrings from said initial character strings by an alignment-based selection.

54. The computer program product of claim 30, wherein the computer code selects at least two substrings from said initial character strings by a frequency-biased selection.

55. A method of identifying molecules for production, wherein the molecules are represented by concatenated strings, said method comprising:
  i) encoding two or more related biological molecules into a data structure of initial character strings to provide a collection of two or more different initial character strings wherein each of said biological molecules comprises at least about 10 subunits;
  ii) selecting at least two substrings from said initial character strings;
  iii) concatenating said substrings to form one or more product strings;
  iv) adding the product strings to a data structure to populate a data structure of product strings; and
  v) determining whether at least one of the product strings have at least a predefined measure of similarity with at least one initial character string; and
  vi) selecting one or more product biological molecules for production, wherein the one or more product biological molecules correspond to one or more of the product strings determined to have greater than the predefined value of sequence identity with at least one initial string.

56. A method of identifying molecules for production, wherein the molecules are represented by concatenated strings, said method comprising:
  i) encoding two or more biological molecules into a data structure of initial character strings to provide a collection of two or more different initial character strings wherein each of said biological molecules comprises at least about 10 subunits;
  ii) selecting at least two substrings from said initial character strings;
  iii) concatenating said substrings to form one or more product strings about the same length as one or more of the initial character strings;
  iv) adding the product strings to a data structure to populate a data structure of product strings;
  v) providing an alignment of at least one of the product strings relative to at least one initial character string; and
  vi) selecting one or more product biological molecules for production, wherein the one or more product biological molecules correspond to one or more of the product strings having greater than 30% sequence identity with the at least one initial character string.

57. The method of claim 56, wherein said encoding comprises encoding two or more amino acid sequences into said character strings, and wherein said two or more amino acid sequences comprise an amino acid sequence encoding a naturally occurring protein.

58. The method of claim 56, wherein said initial character strings have at least 30% sequence identity with each other.

59. The method of claim 56, wherein said selecting in (ii) comprises selecting at least one substring from an initial character string such that the ends of said substring occur in string regions of about 3 to about 20 characters in the initial character string that have higher sequence identity with the corresponding region of another of said initial character strings than the overall sequence identity between the two initial character strings.

60. The method of claim 56, wherein said selecting in (ii) comprises selecting substrings such that the ends of said substrings occur in predefined motifs of about 4 to about 8 characters.

61. The method of claim 56, wherein said selecting in (ii) comprises aligning two or more of said initial character strings to maximize pairwise identity between two or more substrings of the initial character strings, and selecting a character that is a member of an aligned pair for the end of one of the two or more substrings.

62. The method of claim 56, wherein said method further comprises randomly altering one or more characters of said initial or product character strings.

63. The method of claim 56, wherein the one or more product strings of (vi) having greater than 50% sequence identity with the at least one initial character string.

64. The method of claim 56, wherein the one or more product strings of (vi) having greater than 75% sequence identity with the at least one initial character string.

65. The method of claim 56, wherein the one or more product strings of (vi) having greater than 85% sequence identity with the at least one initial character string.

66. The method of claim 56, wherein the one or more product strings of (vi) having greater than 90% sequence identity with the at least one initial character string.

67. The method of claim 56, wherein the one or more product strings of(vi) having greater than 95% sequence identity with the at least one initial character string.

68. The method of claim 56, wherein adding the product strings to a data structure comprises adding more than one product string to the data structure.

69. The method of claim 56, wherein selecting at least two substrings from said initial character strings comprises random substring selection.

70. The method of claim 56, wherein selecting at least two substrings from said initial character strings comprises uniform substring selection.

71. The method of claim 56, wherein selecting at least two substrings from said initial character strings comprises motif-based selection.

72. The method of claim 56, wherein selecting at least two substrings from said initial character strings comprises alignment-based selection.

73. The method of claim 56, wherein selecting at least two substrings from said initial character strings comprises frequency-biased selection.

74. A computer program product on a computer readable media comprising computer code that:
   i) encodes two or more biological molecules into initial character strings to provide a collection of two or more different initial character strings wherein each of said biological molecules comprises at least about ten subunits;
   ii) selects at least two substrings from said initial character strings;
   iii) concatenates said substrings to form one or more product strings about the same length as one or more of the initial character strings;
   iv) adds the product strings to a data structure to populate a data structure of product strings;
   v) provides an alignment of at least one of the product strings relative to at least one initial character string; and
   vi) selects one or more product biological molecules for production, wherein the one or more product biological molecules correspond to one or more of the product strings having greater than 30% sequence identity with the at least one initial character string.

75. The computer program product of claim 74, wherein said computer code encodes two or more amino acid sequences into said character strings, and wherein said two or more amino acid sequences comprise an amino acid sequence encoding a naturally occurring protein.

76. The computer program product of claim 74, wherein said initial character strings have at least 30% sequence identity with each other.

77. The computer program product of claim 74, wherein said computer code selects in (ii) at least one substring from an initial character string such that the ends of said substring occur in string regions of about three to about twenty characters in the initial character string that have higher sequence identity with a corresponding region of another of said initial character strings than the overall sequence identity between the two initial character substrings.

78. The computer program product of claim 74, wherein said computer code selects in (ii) by selecting substrings such that the ends of said substrings occur in predefined motifs of about 4 to about 8 characters.

79. The computer program product of claim 74, wherein said computer code selects in (ii) by aligning two or more of said initial character strings to maximize pairwise identity between two or more substrings of the initial character strings, and selecting a character that is a member of an aligned pair for the end of one of the two or more substrings.

80. The computer program product of claim 74, wherein said computer code further randomly alters one or more characters of said initial or product character strings.

81. The computer program product of claim 74, wherein the one or more product strings of (vi) having greater than 50% sequence identity with the at least one initial character string.

82. The computer program product of claim 74, wherein the one or more product strings of (vi) having greater than 75% sequence identity with the at least one initial character string.

83. The computer program product of claim 74, wherein the one or more product strings of (vi) having greater than 85% sequence identity with the at least one initial character string.

84. The computer program product of claim 74, wherein the one or more product strings of (vi) having greater than 90% sequence identity with the at least one initial character string.

85. The computer program product of claim 74, wherein the one or more product strings of (vi) having greater than 95% sequence identity with the at least one initial character string.

86. The computer program product of claim 74, wherein the computer code adds the product strings to a data structure by adding more than one product string to the data structure.

87. The computer program product of claim 74, wherein the computer code selects at least two substrings from said initial character strings by a random substring selection.

88. The computer program product of claim 74, wherein the computer code selects at least two substrings from said initial character strings by a uniform substring selection.

89. The computer program product of claim 74, wherein the computer code selects at least two substrings from said initial character strings by a motif-based selection.

90. The computer program product of claim 74, wherein the computer code selects at least two substrings from said initial character strings by an alignment-based selection.

91. The computer program product of claim 74, wherein the computer code selects at least two substrings from said initial character strings by a frequency-biased selection.

92. A method of identifying molecules for production, wherein the molecules are represented by concatenated strings, said method comprising:

i) encoding two or more naturally occurring biological molecules into a data structure of initial character strings to provide a collection of two or more different initial character strings wherein each of said biological molecules comprises at least about 10 subunits;

ii) selecting at least two substrings from said initial character strings;

iii) concatenating said substrings to form one or more product strings about the same length as one or more of the initial character strings;

iv) adding the product strings to a data structure to populate a data structure of product strings; and v) selecting one or more product biological molecules for production, wherein the one or more product biological molecules correspond to one or more of the product strings having greater than 30% sequence identity with the at least one initial character string.

93. The method of claim 92, wherein said encoding comprises encoding two or more nucleic acid sequences into said character strings.

94. The method of claim 92, wherein said encoding comprises encoding two or more amino acid sequences into said character strings, and wherein said two or more amino acid sequences comprise an amino acid sequence encoding a naturally occurring protein.

95. The method of claim 92, wherein said initial character strings have at least 30% sequence identity with each other.

96. The method of claim 92, wherein said selecting in (ii) comprises selecting at least one substring from an initial character string such that the ends of said substring occur in string regions of about 3 to about 20 characters in the initial character string that have higher sequence identity with the corresponding region of another of said initial character strings than the overall sequence identity between the two initial character strings.

97. The method of claim 92, wherein said selecting in (ii) comprises selecting substrings such that the ends of said substrings occur in predefined motifs of about 4 to about 8 characters.

98. The method of claim 92, wherein said selecting in (ii) comprises aligning two or more of said initial character strings to maximize pairwise identity between two or more sub strings of the initial character strings, and selecting a character that is a member of an aligned pair for the end of one of the two or more substrings.

99. The method of claim 92, wherein said method further comprises randomly altering one or more characters of said initial or product character strings.

100. The method of claim 92, wherein the one or more product strings of (v) having greater than 50% sequence identity with the at least one initial character string.

101. The method of claim 92, wherein the one or more product strings of (v) having greater than 75% sequence identity with the at least one initial character string.

102. The method of claim 92, wherein the one or more product strings of (v) having greater than 85% sequence identity with the at least one initial character string.

103. The method of claim 92, wherein the one or more product strings of (v) having greater than 90% sequence identity with the at least one initial character string.

104. The method of claim 92, wherein the one or more product strings of (v) having greater than 95% sequence identity with the at least one initial character string.

105. The method of claim 92, wherein adding the product strings to a data structure comprises adding more than one product string to the data structure.

106. The method of claim 92, wherein selecting at least two substrings from said initial character strings comprises random substring selection.

107. The method of claim 92, wherein selecting at least two substrings from said initial character strings comprises uniform substring selection.

108. The method of claim 92, wherein selecting at least two substrings from said initial character strings comprises motif-based selection.

109. The method of claim 92, wherein selecting at least two substrings from said initial character strings comprises alignment-based selection.

110. The method of claim 92, wherein selecting at least two substrings from said initial character strings comprises frequency-biased selection.

111. A computer program product on a computer readable media comprising computer code that:

i) encodes two or more naturally occurring biological molecules into initial character strings to provide a collection of two or more different initial character strings wherein each of said biological molecules comprises at least about ten subunits;

ii) selects at least two substrings from said initial character strings;

iii) concatenates said substrings to form one or more product strings about the same length as one or more of the initial character strings;

iv) adds the product strings to a data structure to populate a data structure of product strings; and v) selects one or more product biological molecules for production, wherein the one or more product biological molecules correspond to one or more of the product strings having greater than 30% sequence identity with the at least one initial character string.

112. The computer program product of claim 111, wherein said computer code encodes by encoding two or more nucleic acid sequences into said character strings.

113. The computer program product of claim 111, wherein said computer code encodes two or more amino acid sequences into said character strings, and wherein said two or more amino acid sequences comprise an amino acid sequence encoding a naturally occurring protein.

114. The computer program product of claim 111, wherein said initial character strings have at least 30% sequence identity with each other.

115. The computer program product of claim 111, wherein said computer code selects in (ii) at least one substring from an initial character string such that the ends of said substring occur in string regions of about three to about twenty characters in the initial character string that have higher sequence identity with a corresponding region of another of said initial character strings than the overall sequence identity between the two initial character substrings.

116. The computer program product of claim 111, wherein said computer code selects in (ii) by selecting substrings such that the ends of said substrings occur in predefined motifs of about 4 to about 8 characters.

117. The computer program product of claim 111, wherein said computer code selects in (ii) by aligning two or more of said initial character strings to maximize pairwise identity between two or more substrings of the initial character strings, and selecting a character that is a member of an aligned pair for the end of one of the two or more substrings.

118. The computer program product of claim 111, wherein said computer code further randomly alters one or more characters of said initial or product character strings.

119. The computer program product of claim 111, wherein the one or more product strings of (v) having greater than 50% sequence identity with the at least one initial character string.

120. The computer program product of claim 111, wherein the one or more product strings of (v) having greater than 75% sequence identity with the at least one initial character string.

121. The computer program product of claim 111, wherein the one or more product strings of (v) having greater than 85% sequence identity with the at least one initial character string.

122. The computer program product of claim 111, wherein the one or more product strings of (v) having greater than 90% sequence identity with the at least one initial character string.

123. The computer program product of claim 111, wherein the one or more product strings of (v) having greater than 95% sequence identity with the at least one initial character string.

124. The computer program product of claim 111, wherein the computer code adds the product strings to a data structure by adding more than one product string to the data structure.

125. The computer program product of claim 111, wherein the computer code selects at least two substrings from said initial character strings by a random substring selection.

126. The computer program product of claim 111, wherein the computer code selects at least two substrings from said initial character strings by a uniform substring selection.

127. The computer program product of claim 111, wherein the computer code selects at least two substrings from said initial character strings by a motif-based selection.

128. The computer program product of claim 111, wherein the computer code selects at least two substrings from said initial character strings by an alignment-based selection.

129. The computer program product of claim 111, wherein the computer code selects at least two substrings from said initial character strings by a frequency-biased selection.

130. A method of identifying molecules for production, wherein the molecules are represented by concatenated strings, said method comprising:
  i) encoding two or more biological molecules into a data structure of initial character strings to provide a collection of two or more different initial character strings wherein each of said biological molecules comprises at least about 10 subunits;
  ii) selecting at least two substrings from said initial character strings;
  iii) concatenating said substrings to form one or more product strings about the same length as one or more of the initial character strings;
  iv) adding the product strings to a data structure to populate a data structure of product strings;
  v) obtaining one or more computationally predicted properties for at least one of the product strings in the data structure; and
  vi) selecting one or more product biological molecules for production on the basis of the one or more computationally predicted properties.

131. The method of claim 130, wherein the computationally predicted properties comprise one or more of a maximum or minimum molecular weight, a maximum or minimum free energy, a maximum or minimum contact surface with a target molecule or surface, a specified net charge, a predicted pK, a predicted pI, a binding avidity, secondary form, and tertiary form.

132. The method of claim 130, wherein said encoding comprises encoding two or more amino acid sequences into said character strings.

133. The method of claim 130, wherein said selecting in (ii) comprises aligning two or more of said initial character strings to maximize pairwise identity between two or more sub strings of the initial character strings, and selecting a character that is a member of an aligned pair for the end of one of the two or more substrings.

134. The method of claim 130, wherein said method further comprises randomly altering one or more characters of said initial or product character strings.

135. The method of claim 130, wherein the one or more product biological molecules of (vi) having greater than 50% sequence identity with the at least one initial character string.

136. The method of claim 130, wherein the one or more product biological molecules of (vi) having greater than 75% sequence identity with the at least one initial character string.

137. The method of claim 130, wherein the one or more product biological molecules of (vi) having greater than 90% sequence identity with the at least one initial character string.

138. The method of claim 130, wherein adding the product strings to a data structure comprises adding more than one product string to the data structure.

139. The method of claim 130, wherein selecting at least two substrings from said initial character strings comprises random substring selection.

140. The method of claim 130, wherein selecting at least two substrings from said initial character strings comprises uniform substring selection.

141. The method of claim 130, wherein selecting at least two substrings from said initial character strings comprises motif-based selection.

142. The method of claim 130, wherein selecting at least two substrings from said initial character strings comprises alignment-based selection.

143. The method of claim 130, wherein selecting at least two substrings from said initial character strings comprises frequency-biased selection.

144. A computer program product on a computer readable media comprising computer code that:
  i) encodes two or more biological molecules into initial character strings to provide a collection of two or more different initial character strings wherein each of said biological molecules comprises at least about ten subunits;
  ii) selects at least two substrings from said initial character strings;
  iii) concatenates said substrings to form one or more product strings about the same length as one or more of the initial character strings;
  iv) adds the product strings to a data structure to populate a data structure of product strings;
  v) obtains one or more computationally predicted properties for at least one of the product strings in the data structure; and
  vi) selects one or more product biological molecules for production on the basis of the one or more computationally predicted properties.

145. The computer program product of claim 144, wherein the computationally predicted properties comprise one or more of a maximum or minimum molecular weight, a maximum or minimum free energy, a maximum or minimum contact surface with a target molecule or surface, a specified net charge, a predicted pK, a predicted pI, a binding avidity, secondary form, and tertiary form.

146. The computer program product of claim 144, wherein the computer code encodes in (i) by encoding two or more amino acid sequences into said character strings.

147. The computer program product of claim 144, wherein the computer code selects in (ii) by aligning two or more of said initial character strings to maximize pairwise identity between two or more substrings of the initial character strings, and selecting a character that is a member of an aligned pair for the end of one of the two or more substrings.

148. The computer program product of claim 144, wherein the computer code further randomly alters one or more characters of said initial or product character strings.

149. The computer program product of claim 144, wherein the one or more product biological molecules of (vi) having greater than 50% sequence identity with the at least one initial character string.

150. The computer program product of claim 144, wherein the one or more product biological molecules of (vi) having greater than 75% sequence identity with the at least one initial character string.

151. The computer program product of claim 144, wherein the one or more product biological molecules of (vi) having greater than 90% sequence identity with the at least one initial character string.

152. The computer program product of claim 144, wherein the computer code adds the product strings to a data structure by adding more than one product string to the data structure.

153. The computer program product of claim 144, wherein the computer code selects at least two substrings from said initial character strings by a random substring selection.

154. The computer program product of claim 144, wherein the computer code selects at least two substrings from said initial character strings by a uniform substring selection.

155. The computer program product of claim 144, wherein the computer code selects at least two substrings from said initial character strings by a motif-based selection.

156. The computer program product of claim 144, wherein the computer code selects at least two substrings from said initial character strings by an alignment-based selection.

157. The computer program product of claim 144, wherein the computer code selects at least two substrings from said initial character strings by a frequency-biased selection.

* * * * *